US007442712B2

(12) United States Patent
Chelliah et al.

(10) Patent No.: US 7,442,712 B2
(45) Date of Patent: Oct. 28, 2008

(54) CONSTRAINED HIMBACINE ANALOGS AS THROMBIN RECEPTOR ANTAGONISTS

(75) Inventors: Mariappan V. Chelliah, Edison, NJ (US); Samuel Chackalamannil, Califon, NJ (US); Yan Xia, Edison, NJ (US); Martin C. Clasby, Plainsboro, NJ (US); William J. Greenlee, Teaneck, NJ (US); Yuguang Wang, North Brunswick, NJ (US); Enrico P. Veltri, Princeton, NJ (US); Wenxue Wu, Princeton Junction, NJ (US); Michael P. Graziano, Scotch Plains, NJ (US); Teddy Kosoglou, Jamison, PA (US); Madhu Chintala, Colts Neck, NJ (US)

(73) Assignee: Schering Corporation, Kenilworth, NJ (US)

( * ) Notice: Subject to any disclaimer, the term of this patent is extended or adjusted under 35 U.S.C. 154(b) by 130 days.

(21) Appl. No.: 11/137,283

(22) Filed: May 25, 2005

(65) Prior Publication Data

US 2005/0267155 A1 Dec. 1, 2005

Related U.S. Application Data

(60) Provisional application No. 60/575,115, filed on May 28, 2004.

(51) Int. Cl.
*A61K 31/44* (2006.01)
*C07D 409/00* (2006.01)
(52) U.S. Cl. .................................. 514/337; 546/284.1
(58) Field of Classification Search .............. 546/284.1; 514/337
See application file for complete search history.

(56) References Cited

U.S. PATENT DOCUMENTS

| 6,063,847 | A  | * | 5/2000  | Chackalamannil et al. | .. 524/297 |
|-----------|----|---|---------|----------------------|------------|
| 6,326,380 | B1 | * | 12/2001 | Chackalamannil et al. | .. 514/311 |
| 6,645,987 | B2 | * | 11/2003 | Chackalamannil et al. | .. 514/337 |
| 6,894,065 | B2 |   | 5/2005  | Chackalamannil et al. |            |
| 7,037,920 | B2 |   | 5/2006  | Chackalamannil et al. |            |
| 7,304,078 | B2 |   | 12/2007 | Chackalamannil et al. |            |
| 2004/0152736 | A1 |  | 8/2004  | Chackalamannil et al. |            |

FOREIGN PATENT DOCUMENTS

WO    WO 1994/03479    2/1994

OTHER PUBLICATIONS

Berge, Stephen M:, et al., "Pharmacuetical Salts", Journal of Pharmaceutical Sciences, 1977, pp. 1-19; vol. 66, issue 1.
Bernatowicz, Michael S., et al., "Development of Potent Thrombin Receptor Antagonist Peptides", J. Med. Chem., 1996, pp. 4879-4887, vol. 39, issue 25.
Chackalamannil, Samuel., et al., "A Highly Efficient Total Synthesis of (+)- Himbacine", J. Am. Chem. Soc., (1996), pp. 9812-9813, vol. 118, issue 40.
Pertwee, Roger G., "Pharmacology of Cannabinoid Receptor Ligands", Current Medicinal Chemistry, 1999, pp. 635-664, vol. 6, issue 8.
International Search Report for International Application No. PCT/US2005/018372, mailed Oct. 26, 2005 (4 pages) for CV06197.

* cited by examiner

*Primary Examiner*—Rei-tsang Shiao
(74) *Attorney, Agent, or Firm*—Gerard E. Reinhardt

(57) ABSTRACT

A compound represented by the structural formula

Formula 1

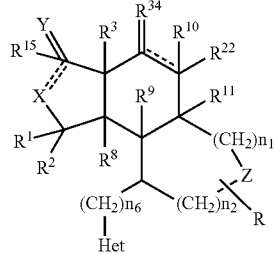

and pharmaceutically acceptable salts and solvents thereof is disclosed, wherein:
the single-dashed line

----- between the ring carbons to which $R^{10}$ and $R^{34}$ are attached represents either a single bond or a double bond;
the double-dashed line

===== between X and the carbon to which Y is attached represents either a single bond or an absent bond;
X is —O— or —NR⁶— when the double-dashed line represents a single bond; X is H, —OH or —NHR²⁰ when the double-dashed line represents an absent bond;
and other parameters are as defined herein.

Also disclosed are pharmaceutical compositions and combinations containing said compounds and their uses as thrombin receptor antagonists and binders to cannabinoid receptors.

15 Claims, No Drawings

CONSTRAINED HIMBACINE ANALOGS AS THROMBIN RECEPTOR ANTAGONISTS

CROSS-REFERENCE TO RELATED APPLICATION

The present application claims priority from U.S. Provisional Application 60/575,115 filed May 28, 2004.

BACKGROUND OF THE INVENTION

A variety of himbacine derivative compounds and pharmaceutical compositions containing these compounds are disclosed in U.S. Pat. Nos. 6,063,847, 6,645,987, and 6,326,380, and U.S. application Ser. Nos. 10/271,715, 10/671,216, and 10/412,982. These himbacine derivatives are useful as thrombin receptor antagonists in the treatment of diseases associated with thrombosis, atherosclerosis, restenosis, hypertension, angina pectoris, arrhythmia, heart failure, cerebral ischemia, stroke, neurodegenerative diseases and cancer. Thrombin receptor antagonists are also known as protease activated receptor-1 (PAR-1) antagonists. Many himbacine derivative compounds also bind to cannabinoid receptors and are useful in the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

Thrombin is known to have a variety of activities in different cell types and thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, 39 (1996), p. 4879-4887, tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor anatgonists are also disclosed in WO 94/03479, published Feb. 17, 1994.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, *Curr. Med. Chem.* 6(8), (1999), 635).

Himbacine, a piperidine alkaloid of the formula

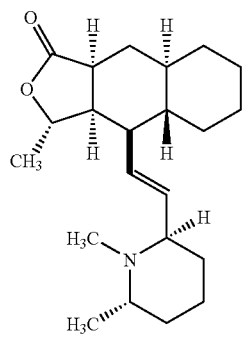

has been identified as a muscarinic receptor antagonist. The total synthesis of (+)-himbacine is disclosed in Chackalamannil et al, *J. Am. Chem Soc.*, 118 (1996), p. 9812-9813.

SUMMARY OF THE INVENTION

In certain aspects, the present invention relates to thrombin receptor antagonists represented by the Formula I

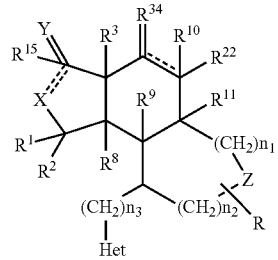

Formula 1 or a pharmaceutically acceptable salt or solvate thereof, wherein:

the single-dashed line

----- between the ring carbons to which $R^{10}$ and $R^{34}$ are attached represents either a single bond or a double bond;

the double-dashed line

===== between X and the carbon to which Y is attached represents either a single bond or an absent bond;

X is —O— or —$NR^6$— when the double-dashed line represents a single bond; X is H, —OH or —$NHR^{20}$ when the double-dashed line represents an absent bond;

$R^{15}$ is H, $C_1$-$C_6$ alkyl, —$NR^{18}R^{19}$ or —$OR^{17}$ when the double-dashed line represents an absent bond; or $R^{15}$ is H or $C_1$-$C_6$ alkyl when Y is

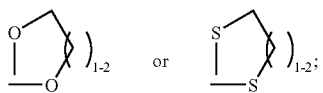

$R^{15}$ is absent when the double-dashed line represents a single bond;

Y is (O), (S), (H, H), (H, OH) or (H, $C_1$-$C_6$ alkoxy) when the double-dashed line represents a single bond; Y is (O), (NOR$^{17}$), (H, H), (H, OH), (H, SH), (H, $C_1$-$C_6$ alkoxy) or (H, —NHR$^{45}$) when the double-dashed line represents an absent bond;

Z is selected from the group consisting of —CH$_2$—, —O—, —S(O)$_{n4}$—, —NR$^{30}$—, —NC(O)R$^{30}$, NCOR$^{30}$—, —NC(O)NR$^3$OR$^3$—, —NSO$_2$R—, —NSO$_2$NHR$^+$—, —C(O)—, —C(=NOR$^{30}$)—, and —CR$^{30}$R$^{31}$—;

$n_1$, $n_2$, $n_3$ and $n_4$ are independently 0-2;

R is 1 to 3 substituents independently selected from the group consisting of H, $C_1$-$C_6$ alkyl, halogen, hydroxy, amino, ($C_1$-$C_6$) alkyl-amino, ($C_1$-$C_6$)dialkylamino, ($C_1$-$C_6$)alkoxy, —COR$^{16}$, —COOR$^{17}$, —SOR$^{16}$, —SO$_2$R$^{16}$, —NR$^{16}$COR$^{16a}$, —NR$^{16}$COOR$^{16a}$, —NR$^{16}$CONR$^4$R$^5$, fluoro-($C_1$-$C_6$)alkyl, difluoro($C_1$-$C_6$)alkyl, trifluoro($C_1$-$C_6$)alkyl, $C_3$-$C_6$ cycloalkyl, $C_2$-$C_6$ alkenyl, aryl($C_1$-$C_6$)alkyl, aryl($C_2$-$C_6$)alkenyl, heteroaryl($C_1$-$C_6$)-alkyl, heteroaryl($C_2$-$C_6$)alkenyl, hydroxy($C_1$-$C_6$)alkyl, amino($C_1$-$C_6$)-alkyl, aryl and thio($C_1$-$C_6$)alkyl;

$R^1$ and $R^2$ are independently selected from the group consisting of H, $C_1$-$C_6$ alkyl, fluoro($C_1$-$C_6$)alkyl, difluoro ($C_1$-$C_6$)alkyl, trifluoro-($C_1$-$C_6$)alkyl, $C_3$-$C_7$ cycloalkyl, $C_2$-$C_6$ alkenyl, aryl($C_1$-$C_6$)alkyl, aryl($C_2$-$C_6$)alkenyl, heteroaryl($C_1$-$C_6$)alkyl, heteroaryl($C_2$-$C_6$)alkenyl, hydroxy-($C_1$-$C_6$)alkyl, ($C_1$-$C_6$)alkoxy($C_1$-$C_6$)alkyl, amino-($C_1$-$C_6$)alkyl, aryl and thio($C_1$-$C_6$)alkyl; or $R^1$ and $R^2$ together form a =O group;

$R^3$ is H, hydroxy, $C_1$-$C_6$ alkoxy, —NR$^{18}$R$^{19}$, —SOR$^{16}$, —SO$_2$R$^{17}$, —C(O)OR$^{17}$, —C(O)NR$^{18}$R$^{19}$, $C_1$-$C_6$ alkyl, halogen, fluoro($C_1$-$C_6$)alkyl, difluoro($C_1$-$C_6$)alkyl, trifluoro($C_1$-$C_6$)alkyl, $C_3$-$C_7$ cycloalkyl, $C_2$-$C_6$ alkenyl, aryl($C_1$-$C_6$)alkyl, aryl($C_2$-$C_6$)alkenyl, heteroaryl($C_1$-$C_6$)alkyl, heteroaryl($C_2$-$C_6$)alkenyl, hydroxy($C_1$-$C_6$) alkyl, amino($C_1$-$C_6$)alkyl, aryl, thio($C_1$-$C_6$)alkyl, ($C_1$-$C_6$)alkoxy($C_1$-$C_6$)alkyl or ($C_1$-$C_6$)alkylamino($C_1$-$C_6$) alkyl, —O-aryl, N$_3$, NO$_2$, C(=NR$^1$)NR$^1$R$^2$, N=C(R$^1$) NR$^1$R$^2$, NR$^{18}$COR$^{19}$, NR$^{18}$CONR$^{18}$R$^{19}$, NR$^{18}$C(O) OR$^{19}$, NR$^{18}$S(O)$_2$R$^{19}$, NR$^{18}$S(O)$_2$NR$^{18}$R$^{19}$, NHNR$^{18}$R$^9$, NR$^{18}$NR$^{18}$R$^{19}$ or NR$^{18}$R$^{19}$;

Het is a mono-, bi- or tricyclic heteroaromatic group of 5 to 14 atoms comprised of 1 to 13 carbon atoms and 1 to 4 heteroatoms independently selected from the group consisting of N, O and S, wherein a ring nitrogen can form an N-oxide or a quaternary group with a $C_1$-$C_4$ alkyl group, wherein the Het group is optionally substituted by 1 to 4 moieties, W, independently selected from the group consisting of H; $C_1$-$C_6$ alkyl; fluoro($C_1$-$C_6$)alkyl; difluoro ($C_1$-$C_6$)alkyl; trifluoro-($C_1$-$C_6$)-alkyl; $C_3$-$C_7$ cycloalkyl; heterocycloalkyl; heterocycloalkyl substituted by $C_1$-$C_6$ alkyl, $C_2$-$C_6$ alkenyl, OH—($C_1$-$C_6$)alkyl, or =O; $C_2$-$C_6$ alkenyl; R$^{21}$-aryl($C_1$-$C_6$)alkyl; R$^{21}$-aryl-($C_2$-$C_6$)-alkenyl; R$^{21}$-aryloxy; R$^{21}$-aryl-NH—; heteroaryl($C_1$-$C_6$) alkyl; heteroaryl($C_2$-$C_6$)-alkenyl; heteroaryloxy; heteroaryl-NH—; hydroxy($C_1$-$C_6$)alkyl; dihydroxy($C_1$-$C_6$)alkyl; amino($C_1$-$C_6$)alkyl; ($C_1$-$C_6$)alkylamino-($C_1$-$C_6$)alkyl; di-(($C_1$-$C_6$)alkyl)-amino($C_1$-$C_6$)alkyl; thio ($C_1$-$C_6$)alkyl; $C_1$-$C_6$ alkoxy; $C_2$-$C_6$ alkenyloxy; halogen; —NR$^4$R$^5$; —CN; —OH; —COOR$^{17}$; —COR$^{16}$; —OSO$_2$CF$_3$; —CH$_2$OCH$_2$CF$_3$; ($C_1$-$C_6$) alkylthio; —C(O)NR$^4$R$^5$; —OCHR$^6$-phenyl; phenoxy-($C_1$-$C_6$)alkyl; —NHCOR$^{16}$; —NHSO$_2$R$^{16}$; biphenyl; —OC(R$^6$)$_2$COOR$^7$; —OC(R$^6$)$_2$C(O)NR$^4$R$^5$; ($C_1$-$C_6$) alkoxy; —C(=NOR$^{17}$)R$^{18}$; $C_1$-$C_6$ alkoxy substituted by ($C_1$-$C_6$)alkyl, amino, —OH, COOR$^{17}$, —NH-COOR$^{17}$, —CONR$^4$R$^5$, aryl, aryl substituted by 1 to 3 substutuents independently selected from the group consisting of halogen, —CF$_3$, $C_1$-$C_6$ alkyl, $C_1$-$C_6$ alkoxy and —COOR$^{17}$, aryl wherein adjacent carbons form a ring with a methylenedioxy group, —C(O)NR$^4$R$^5$ or heteroaryl; R$^{21}$-aryl; aryl wherein adjacent carbons form a ring with a methylenedioxy group; R$^{41}$-heteroaryl; and heteroaryl wherein adjacent carbon atoms form a ring with a $C_3$-$C_5$ alkylene group or a methylenedioxy group;

$R^4$ and $R^5$ are independently selected from the group consisting of H, $C_1$-$C_6$ alkyl, phenyl, benzyl and $C_3$-$C_7$ cycloalkyl, or $R^4$ and $R^5$ together are —(CH$_2$)$_4$—, —(CH$_2$)$_5$— or —(CH$_2$)$_2$NR$^7$—(CH$_2$)$_2$— and form a heterocyclyl ring with the nitrogen to which they are attached;

$R^6$ is independently selected from the group consisting of H, $C_1$-$C_6$ alkyl, phenyl, ($C_3$-$C_7$)cycloalkyl, ($C_3$-$C_7$)cycloalkyl($C_1$-$C_6$)alkyl, ($C_1$-$C_6$)alkoxy($C_1$-$C_6$)alkyl, hydroxy($C_1$-$C_6$)alkyl and amino($C_1$-$C_6$)alkyl;

$R^7$ is H or ($C_1$-$C_6$)alkyl;

$R^8$, $R^{10}$ and $R^{11}$ are independently selected from the group consisting of $R^1$ and —OR$^1$, provided that when the single-dashed line is a double bond, $R^{10}$ is absent;

$R^9$ is H, OH, $C_1$-$C_6$ alkoxy, halogen or halo($C_1$-$C_6$)alkyl;

$R^{16}$ and $R^{16a}$ are independently selected from the group consisting of $C_1$-$C_6$ lower alkyl, phenyl or benzyl;

$R^{17}$, $R^{18}$ and $R^{19}$ are independently selected from the group consisting of H, $C_1$-$C_6$ alkyl, phenyl, benzyl;

$R^{20}$ is H, $C_1$-$C_6$ alkyl, phenyl, benzyl, —C(O)R$^6$ or —SO$_2$R$^6$;

$R^{21}$ is 1 to 3 moieties independently selected from the group consisting of H, —CN, —CF$_3$, —OCF$_3$, halogen, —NO$_2$, $C_1$-$C_6$ alkyl, $C_1$-$C_6$alkoxy, ($C_1$-$C_6$)alkylamino, di-(($C_1$-$C_6$)alkyl)amino, amino($C_1$-$C_6$)alkyl, ($C_1$-$C_6$)-alkylamino($C_1$-$C_6$)alkyl, di-(($C_1$-$C_6$)alkyl)-amino($C_1$-$C_6$)alkyl, hydroxy-($C_1$-$C_6$)alkyl, —COOR$^1$ 7, —COR$^{17}$, —NHCOR$^{16}$, —NHSO$_2$R$^{16}$, —NHSO$_2$CH$_2$CF$_3$, heteroaryl, —C(=NOR$^7$)R$^{18}$, NR$^{25}$R$^{26}$ alkyl-, hydroxy-alkyl-, —C(O)OR$^{17}$, —COR$^{17}$, —NHCOR$^{16}$, —NHS(O)$_2$R$^{16}$, —NHS(O)$_2$ CH$_2$CF$_3$, —C(O)NR$^{25}$R$^{26}$—NR$^{25}$—C(O)—NR$^{25}$R$^{26}$, —S(O)R$^{13}$, —S(O)$_2$R and —SR$^{13}$;

$R^{22}$ is selected from the group consisting of H, R$^{24}$—($C_1$-$C_{10}$)alkyl, R$^{24}$—($C_2$-$C_{10}$)alkenyl, R$^{24}$—($C_2$-$C_{10}$)alkynyl, R$^{27}$-hetero-cycloalkyl, R$^{25}$-aryl, R$^{25}$-aryl($C_1$-$C_6$) alkyl, R$^{29}$—($C_3$-$C_7$)cycloalkyl, R$^{29}$—($C_3$-$C_7$) cycloalkenyl, —OH, —OC(O)R$^{30}$, —C(O)OR$^{30}$, —C(O)R$^{30}$, —C(O)NR$^{30}$R$^{31}$, —NR$^{30}$R$^{31}$, —NR$^{30}$C (O)R$^{31}$—NR$^{30}$C(O)NR$^{31}$R$^{32}$, NHSO$_2$R$^{30}$, —OC(O) NR$^{30}$R$^{31}$, R$^{24}$—($C_1$-$C_{10}$)alkoxy, R$^{24}$—($C_2$-$C_{10}$)-alkenyloxy, R$^{24}$—($C_2$-$C_{10}$)alkynyloxy, R$^{27}$-heterocycloalkyloxy, R$^{29}$—($C_3$-$C_7$)cycloalkyloxy, R$^{29}$—($C_3$-$C_7$)cyclo-alkenyloxy, R$^{29}$—($C_3$-$C_7$)cycloalkyl-NH—, —NHSO$_2$NHR$^{16}$ and —CH (=NOR$^{17}$);

or $R^{22}$ and $R^{10}$ together with the carbon to which they are attached, independently form a R$^{42}$-substituted carbocyclic ring of 3-10 atoms, or a $R^{42}$-substituted heterocyclic ring of 4-10 atoms wherein 1-3 ring members are independently selected from the group consisting of —O—, —NH— and —SOn$_2$-, provided that when $R^{22}$ and $R^{10}$ form a ring, the single-dashed line represents an absent bond;

$R^{24}$ is 1, 2 or 3 moieties independently selected from the group consisting of H, halogen, —OH, $(C_1-C_6)$alkoxy, $R^{35}$-aryl, $(C_1-C_{10})$-alkyl-C(O)—, $(C_2-C_{10})$-alkenyl-C(O)—, $(C_2-C_{10})$alkynyl-C(O), heterocycloalkyl, $R^{26}$—$(C_3-C_7)$cycloalkyl, $R^{26}$—$(C_3-C_7)$cycloalkenyl, —OC(O)$R^{30}$, —C(O)O$R^{30}$, —C(O)$R^{30}$—C(O)N$R^3$O$R^3$, N$R^3$O$R^3$—N$R^{30}$C(O)$R^{31}$, N$R^{30}$C(O)N$R^{31}$$R^{32}$—NHSO$_2$$R^{30}$, —OC(O)N$R^{31}$$R^{31}$, $R^{24}$—$(C_2-C_{10})$-alkenyloxy, $R^{24}$—$(C_2-C_{10})$alkynyloxy, $R^{27}$-heterocycloalkyloxy, $R^{29}$—$(C_3-C_7)$-cycloalkyloxy, $R^{29}$—$(C_3-C_7)$cyclo-alkenyloxy, $R^{29}$—$(C_3-C_7)$cycloalkyl-NH—, —NHSO$^2$NH$R^{16}$ and —CH(=NO$R^{17}$);

$R^{25}$ is 1, 2 or 3 moieties independently selected from the group consisting of H, heterocycloalkyl, halogen, —COO$R^{36}$, —CN, —C(O)N$R^{37}$$R^{38}$, —N$R^{39}$C(O)$R^{40}$, —O$R^{36}$, $(C_3-C_7)$cycloalkyl, $(C_3-C_7)$cycloalkyl-$C_1-C_6$)alkyl, $(C_1-C_6)$alkyl$(C_3-C_7)$cycloalkyl-$(C_1-C_6)$alkyl, halo$(C_1-C_6)$alkyl$(C_3-C_7)$cycloalkyl$(C_1-C_6)$alkyl, hydroxy$(C_1-C_6)$alkyl, $(C_1-C_6)$alkoxy$(C_1-C_6)$alkyl, and $R^{41}$-heteroaryl; or two $R^{25}$ groups on adjacent ring carbons form a fused methylenedioxy group;

$R^{26}$ is 1, 2, or 3 moieties independently selected from the group consisting of H, halogen and $(C_1-C_6)$ alkoxy;

$R^{27}$ is 1, 2 or 3 moieties independently selected from the group consisting of H, $R^{28}$—$(C_1-C_{10})$alkyl, $R^{28}$—$(C_2-C_{10})$alkenyl, and $R^{28}$—$(C_2-C_{10})$alkynyl;

$R^{28}$ is H, —OH or $(C_1-C_6)$ alkoxy;

$R^{29}$ is 1, 2 or 3 moieties independently selected from the group consisting of H, $(C_1-C_6)$alkyl, —OH, $(C_1-C_6)$alkoxy and halogen;

$R^{30}$, $R^{31}$ and $R^{32}$ are independently selected from the group consisting of H, $(C_1-C_{10})$-alkyl, $(C_1-C_6)$alkoxy$(C_1-C_{10})$-alkyl, $R^{25}$-aryl$(C_1-C_6)$-alkyl, $R^{33}$—$(C_3-C_7)$cycloalkyl, $R^{34}$—$(C_3-C_7)$cycloalkyl$(C_1-C_6)$alkyl, $R^{25}$-aryl, heterocycloalkyl, heteroaryl, heterocycloalkyl$(C_1-C_6)$alkyl and heteroaryl$(C_1-C_6)$alkyl;

$R^{33}$ is H, $(C_1-C_6)$alkyl, OH—$(C_1-C_6)$alkyl or $(C_1-C_6)$alkoxy;

$R^{34}$ is (H, $R^3$), (H, $R^{43}$), (O) or (NO$R^{17}$) when the single-dashed line is a single bond; $R^{34}$ is $R^{44}$ when the single-dashed line is a double bond;

$R^{35}$ is 1 to 4 moieties independently selected from the group consisting of H, $(C_1-C_6)$alkyl, —OH, halogen, —CN, $(C_1-C_6)$alkoxy, trihalo$(C_1-C_6)$alkoxy, $(C_1-C_6)$alkylamino, di$((C_1-C_6)$alkyl)amino, —OCF$_3$, OH—$(C_1-C_6)$alkyl, —CHO, —C(O)$(C_1-C_6)$-alkylamino, —C(O)di$((C_1-C_6)$alkyl)amino, —NH$_2$, —NHC(O)$(C_1-C_6)$alkyl and —N$((C_1-C_6)$alkyl)C(O)$(C_1-C_6)$alkyl;

$R^{36}$ is H, $(C_1-C_6)$alkyl, halo$(C_1-C_6)$alkyl, dihalo$(C_1-C_6)$alkyl or trifluoro$(C_1-C_6)$alkyl;

$R^{37}$ and $R^{38}$ are independently selected from the group consisting of H, $(C_1-C_6)$alkyl, aryl$(C_1-C_6)$alkyl, phenyl and $(C_3-C_{15})$cycloalkyl; or $R^{37}$ and $R^{38}$ together are —$(CH_2)_4$—, —$(CH_2)_5$— or —$(CH_2)_2$—N$R^{39}$—$(CH_2)_2$— and form a ring with the nitrogen to which they are attached;

$R^{39}$ and $R^{40}$ are independently selected from the group consisting of H, $(C_1-C_6)$alkyl, aryl$(C_1-C_6)$alkyl, phenyl and $(C_3-C_{15})$-cycloalkyl;

or $R^{39}$ and $R^{40}$ in the group —N$R^{39}$C(O)$R^{40}$, together with the carbon and nitrogen atoms to which they are attached, form a cyclic lactam having 5-8 ring members;

$R^{41}$ is 1 to 4 moieties independently selected from the group consisting of H, $(C_1-C_6)$alkyl, $(C_1-C_6)$alkoxy, $(C_1-C_6)$alkylamino, di$((C_1-C_6)$alkyl)amino, —OCF$_3$, OH—$(C_1-C_6)$alkyl, —CHO and phenyl;

$R^{42}$ is 1 to 3 moieties independently selected from the group consisting of hydrogen, —OH, $(C_1-C_6)$alkyl and $(C_1-C_6)$alkoxy;

R is —N$R^{30}$$R^{31}$, —N$R^{30}$C(O)$R^{31}$, —N$R^{30}$C(O)N$R^{31}$$R^{32}$, —NHSO$_2$$R^{30}$ or —NHCOO$R^{17}$;

$R^{44}$ is H, $C_1-C_6$ alkoxy, —SO$R^{16}$, —SO$_2$$R^{17}$, —C(O)O$R^{17}$, —C(O)N$R^{18}$$R^{19}$, $C_1-C_6$ alkyl, halogen, fluoro$(C_1-C_6)$alkyl, difluoro$(C_1-C_6)$alkyl, trifluoro$(C_1-C_6)$alkyl, $C_3-C_7$ cycloalkyl, $C_2-C_6$ alkenyl, aryl$(C_1-C_6)$alkyl, aryl$(C_2-C_6)$alkenyl, heteroaryl$(C_1-C_6)$alkyl, heteroaryl$(C_2-C_6)$alkenyl, hydroxy$(C_1-C_6)$alkyl, amino$(C_1-C_6)$alkyl, aryl, thio$(C_1-C_6)$alkyl, $(C_1-C_6)$alkoxy$(C_1-C_6)$alkyl or $(C_1-C_6)$alkylamino$(C_1-C_6)$alkyl; and $R^{45}$ is H, $C_1-C_6$ alkyl, —COO$R^{16}$ or —SO$_2$.

In certain embodiments, Het is pyridyl and W is phenyl.

In further embodiments, W is substituted by fluoro or —CN.

In yet further embodiments, Z is —CH$_2$—, $n_1$ is 1, $n_2$ is 0, and $n_3$ is 1.

In yet further embodiments, Z is —O—, $n_1$ is 1, $n_2$ is 0, and $n_3$ is 1.

In yet further embodiments, Z is —O—, $n_1$ is 2, $n_2$ is 0, and $n_3$ is 1.

In yet further embodiments, $R^1$ is methyl, and $R^2$, $R^8$, $R^9$, $R^{10}$, $R^{11}$ are all H.

In yet further embodiments, $R^3$ is H.

In yet further embodiments, $R^3$ is —OH.

In yet further embodiments, $R^{22}$ is methyl.

In yet further embodiments, X and Y are both O.

In yet further embodiments, the single-dashed line and double-dashed line are both single bonds.

In yet further embodiments, the invention is directed to a pharmaceutical composition comprising a therapeutically effective amount of at least one compound of Formula I and a pharmaceutically acceptable carrier.

In yet further embodiments, the invention is directed to a method of inhibiting thrombin receptors comprising administering to a mammal in need of such treatment a therapeutically effective amount of at least one compound of Formula I.

In yet further embodiments, the invention is directed to a method of inhibiting cannabinoid receptors comprising administering to a mammal in need of such treatment a therapeutically effective amount of at least one compound of Formula I.

In yet further embodiments, the invention is directed to a method of treating a therapeutic condition comprising administering to a mammal in need of such treatment a therapeutically effective amount of at least one compound of Formula I wherein said therapeutic condition is a cardiovascular or circulatory disease or condition, an inflammatory disease or condition, a respiratory tract disease or condition, cancer, acute renal failure, glomerulonephritis, astrogliosis, a fibrotic disorder of the liver, kidney, lung or intestinal tract, Alzheimer's disease, diabetes, diabetic neuropathy, rheumatoid arthritis, neurodegenerative disease, neurotoxic disease, systemic lupus erythematosus, multiple sclerosis, osteoporosis, glaucoma, macular degeneration, psoriasis, radiation fibrosis, endothelial dysfunction, a wound or a spinal cord injury, or a symptom or result thereof.

In yet further embodiments, the invention is directed to a method of treating a therapeutic condition wherein the cardiovascular or circulatory disease or condition is atherosclerosis, restenosis, hypertension, acute coronary syndrome, angina pectoris, arrhythmia, heart disease, heart failure, myocardial infarction, thrombotic or thromboembolytic stroke, a peripheral vascular disease, deep vein thrombosis, venous thromboembolism, a cardiovascular disease associated with hormone replacement therapy, disseminated intravascular coagulation syndrome, renal ischemia, cerebral stroke, cerebral ischemia, cerebral infarction, migraine, renal vascular homeostasis or erectile dysfunction.

In yet further embodiments, the invention is directed to a method of treating a therapeutic condition wherein the inflammatory disease or condition is irritable bowel syndrome, Crohn's disease, nephritis or a radiation- or chemotherapy-induced proliferative or inflammatory disorder of the gastrointestinal tract, lung, urinary bladder, gastrointestinal tract or other organ.

In yet further embodiments, the invention is directed to a method of treating a therapeutic condition wherein the respiratory tract disease or condition is reversible airway obstruction, asthma, chronic asthma, bronchitis or chronic airways disease.

In yet further embodiments, the invention is directed to a method of treating a therapeutic condition wherein the cancer is renal cell carcinoma or an angiogenesis related disorder.

In yet further embodiments, the invention is directed to a method of treating a therapeutic condition wherein the neurodegenerative disease is Parkinson's disease, amyotropic lateral sclerosis, Alzheimer's disease, Huntington's disease or Wilson's disease.

In yet further embodiments, the invention is directed to a method of treating a therapeutic condition further comprising administering at least one therapeutically effective agent useful in the treatment of inflammation, rheumatism, asthma, glomerulonephritis, osteoporosis, neuropathy and/or malignant tumors, angiogenesis related disorders, cancer, disorders of the liver, kidney or lung, melanoma, renal cell carcinoma, renal disease, acute renal failure, chronic renal failure, renal vascular homeostasis, glomerulonephritis, chronic airways disease, bladder inflammation, neurodegenerative and/or neurotoxic diseases, conditions, or injuries, radiation fibrosis, endothelial dysfunction, periodontal diseases or wounds.

In yet further embodiments, the invention is directed to a method of treating a therapeutic condition further comprising administering at least two therapeutically effective agents.

DETAILED DESCRIPTION

This invention relates to the discovery of compounds represented by Formula I as thrombin receptor antagonists. These compounds and any formulations containing them can be useful for the treatment of a variety of diseases and conditions, including but not limited to thrombosis, atherosclerosis, cardiac arrhythmia, heart failure, restenosis, angina pectoris, hypertension, cerebral ischemia, cancer, cerebral stroke, multiple sclerosis, diabetes, osteoporosis, rheumatoid arthritis, systemic lupus erythematous, renal ischemia nephritis, inflammatory diseases of the lungs and gastrointestinal tract, and respiratory tract disorders such as reversible airway obstruction, chronic asthma, and bronchitis.

In Formula I, when $R^4$ and $R^5$ join to form a ring with the nitrogen to which they are attached, the rings formed are 1-pyrrolidinyl, 1-piperidinyl and 1-piperazinyl, wherein the piperazinyl ring may also be optionally substituted at the 4-position nitrogen by a group $R^7$.

When the single-dashed ring bond in the moiety:

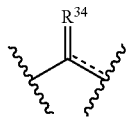

represents a single bond, $R^{34}$ is (O) or (N)(O)($R^{17}$), or (H)($R^3$) or (H)($R^{43}$). Similarly, when the single-dashed ring bond in the moiety:

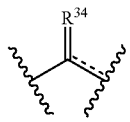

represents a double bond, $R^{34}$ is $R^{44}$.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

Fluoroalkyl, difluoroalkyl and trifluoroalkyl mean alkyl chains wherein the terminal carbon is substituted by 1, 2 or 3 fluoroatoms, e.g., —CF$_3$, —CH$_2$CF$_3$, —CH$_2$CHF$_2$ or —CH$_2$CH$_2$F. Haloalkyl means an alkyl chain substituted by 1 to 3 halo atoms.

"Alkenyl" means straight or branched carbon chains of carbon atoms having one or more double bonds in the chain, conjugated or unconjugated. "Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

Substitution on alkyl, alkenyl and alkynyl chains depends on the length of the chain, and the size and nature of the substituent. Those skilled in the art will appreciate that while longer chains can accommodate multiple substituents, shorter alkyl chains, e.g., methyl or ethyl, can have multiple substitution by halogen, but otherwise are likely to have only one or two substituents other than H. Shorter unsaturated chains, e.g., ethenyl or ethynyl, are generally unsubstituted or substitution is limited to one or two groups, depending on the number of available carbon bonds.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkylene" refers to a corresponding bivalent ring, wherein the points of attachment to other groups include all positional and stereoisomers. "Cycloalkenyl" refers to a carbon ring of 3 to 7 atoms and having one or more unsaturated bonds, but not having an aromatic nature.

"Ring system substituent" means a substituent attached to an aromatic or non-aromatic ring system which, for example, replaces an available H on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of H, alkyl, aryl, cycloalkyl, and aralkyl. "Ring system substituent" may also mean a single moiety which simultaneously replaces two available Hs on two adjacent carbon atoms (one H on each carbon) on a ring system. Examples of such moiety are methylene dioxy, ethylenedioxy, —C(CH$_3$)$_2$— and the like which form moieties such as, for example:

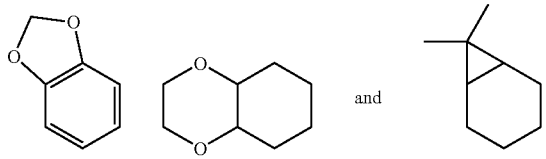

"Heterocycloalkyl" means saturated rings of 5 or 6 atoms comprised of 4 to 5 carbon atoms and 1 or 2 heteroatoms selected from the group consisting of —O—, —S— and —NR$^7$— joined to the rest of the molecule through a carbon atom. Examples of heterocycloalkyl groups are 2-pyrrolidinyl, tetrahydrothiophen-2-yl, tetrahydro-2-furanyl, 4-piperidinyl, 2-piperazinyl, tetrahydro-4-pyranyl, 2-morpholinyl and 2-thiomorpholinyl.

"Halogen" refers to fluorine, chlorine, bromine or iodine radicals.

"Dihydroxy(C$_1$-C$_6$)alkyl" refers to an alkyl chain substituted by two hydroxy groups on two different carbon atoms.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl, naphthyl, indenyl, tetrahydronaphthyl or indanyl.

"Heteroaryl" means a single ring or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included, as well as compounds wherein a ring nitrogen is substituted by a C$_1$-C$_4$ alkyl group to form a quaternary amine. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl. W-substituted heteroaryl refers to such groups wherein substitutable ring carbon atoms have a substituent as defined above, or where adjacent carbon atoms form a ring with an alkylene group or a methylenedioxy group, or where a nitrogen in the Het ring can be substituted with R$^{21}$-aryl or an optionally substituted alkyl substituent as defined in W.

The term "Het" is exemplified by the single ring and benzofused heteroaryl groups as defined immediately above, as well as tricyclic groups such as benzoquinolinyl (e.g., 1,4 or 7,8) and phenanthrolinyl (e.g., 1,7; 1, 10; or 4,7).

Examples of heteroaryl groups wherein adjacent carbon atoms form a ring with an alkylene group are 2,3-cyclopentenopyridine, 2,3-cyclohexenopyridine and 2,3-cycloheptenopyridine.

The above statements, wherein, for example, R$^4$ and R$^5$ are said to be independently selected from a group of substituents, means that R$^4$ and R$^5$ are independently selected, but also that where an R$^4$ or R$^5$ variable occurs more than once in a molecule, those occurrences are independently selected. Those skilled in the art will recognize that the size and nature of the substituent(s) will affect the number of substituents that can be present.

The term "substituted" means that one or more Hs on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties. The optionally substituted atom may be either unsubstituted, or substituted as indicated.

Compounds of the invention have at least one asymmetrical carbon atom and therefore all isomers, including diastereomers and rotational isomers are contemplated as being part of this invention. The invention includes (+)- and (−)-isomers in both pure form and in admixture, including racemic mixtures. Isomers can be prepared using conventional techniques, either by reacting optically pure or optically enriched starting materials or by separating isomers of a compound of Formula I.

It should also be noted that any carbon as well as heteroatom with unsatisfied valences in the text, schemes and examples herein is assumed to have the sufficient number of H atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the thrombin receptors and thus producing the desired therapeutic, ameliorative, inhibitory or preventative effect.

Those skilled in the art will appreciate that for some compounds of Formula I, one isomer will show greater pharmacological activity than other isomers.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

It should be understood that the invention encompasses embodiments comprising a compound of Formula I, as well as combinations of at least one compound of Formula I and at least one salt or solvate of a compound of Formula I.

It should further be understood that unless otherwise stated, all quantitative measures, e.g., of time, temperature, mass and volume, include a reasonable scope of variation and are not to be limited to their nominal stated values.

The synthesis of representative compounds of Forumla I is presented below.

In Scheme 1, the heterohimbacine analog 1 was cleaved with $BBr_3$ followed by protection of the resultant alcohol to provide the acetate 2. Intramolecular free radical cyclization of this analog provided compound 3 which was treated with methanolic $K_2CO_3$ to provide alcohol 4. The alcohol was deoxygenated and a 7a-hydroxy group was introduced to provide 5. It was also converted to the oxime ether 6.

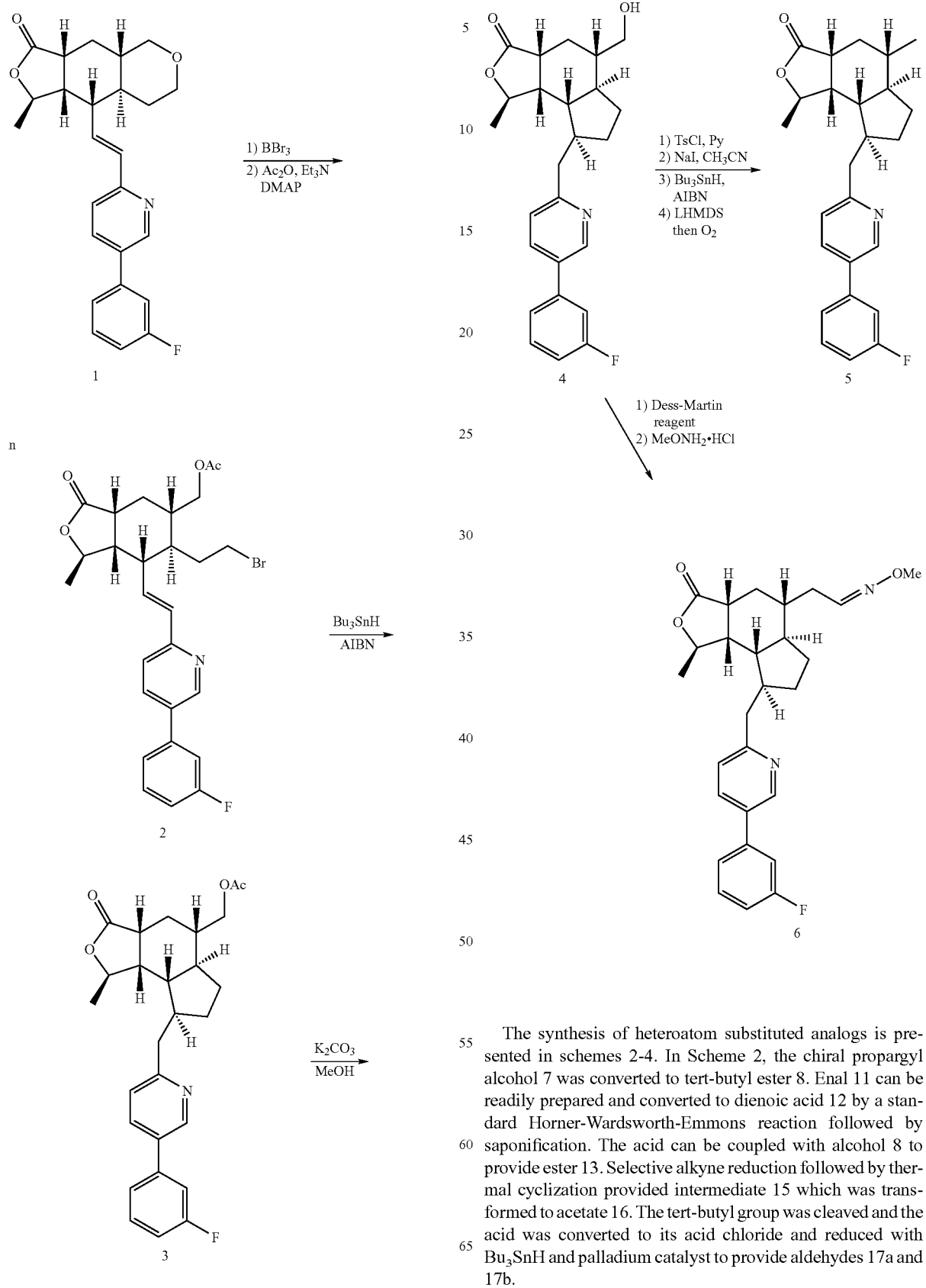

The synthesis of heteroatom substituted analogs is presented in schemes 2-4. In Scheme 2, the chiral propargyl alcohol 7 was converted to tert-butyl ester 8. Enal 11 can be readily prepared and converted to dienoic acid 12 by a standard Horner-Wardsworth-Emmons reaction followed by saponification. The acid can be coupled with alcohol 8 to provide ester 13. Selective alkyne reduction followed by thermal cyclization provided intermediate 15 which was transformed to acetate 16. The tert-butyl group was cleaved and the acid was converted to its acid chloride and reduced with Bu₃SnH and palladium catalyst to provide aldehydes 17a and 17b.

Scheme 2
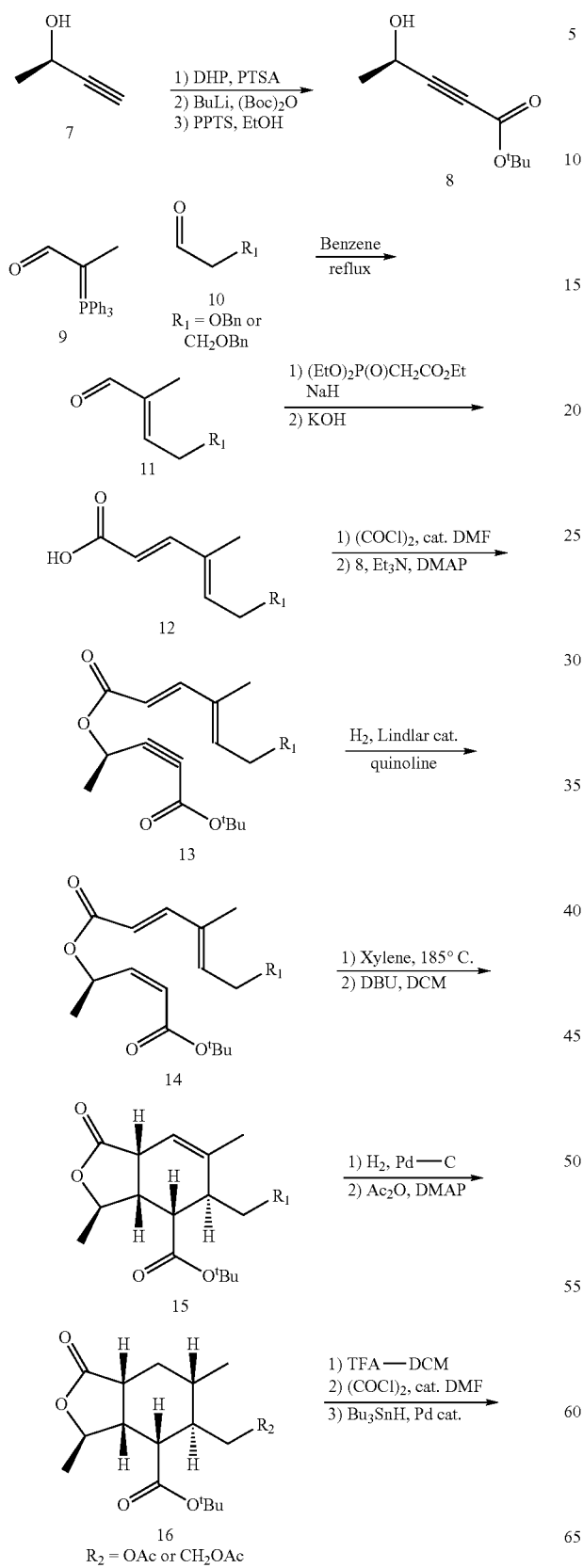
In Scheme 3, Aldehyde 17a was coupled with phosphonate 18 to provide intermediate 19. When this compound was refluxed with methanolic $K_2CO_3$ it provided the cyclic ether 20 which was hydroxylated at 7a-position to provide intermediate 21. This intermediate was coupled with boronic acids to provide analogs 22a-d.
Scheme 3
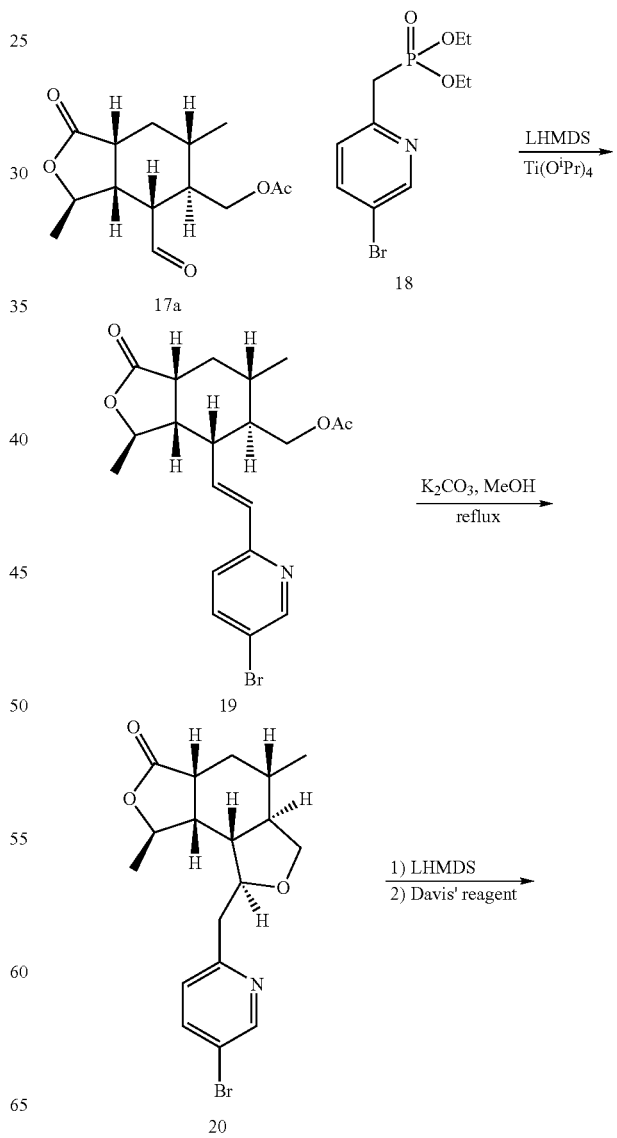

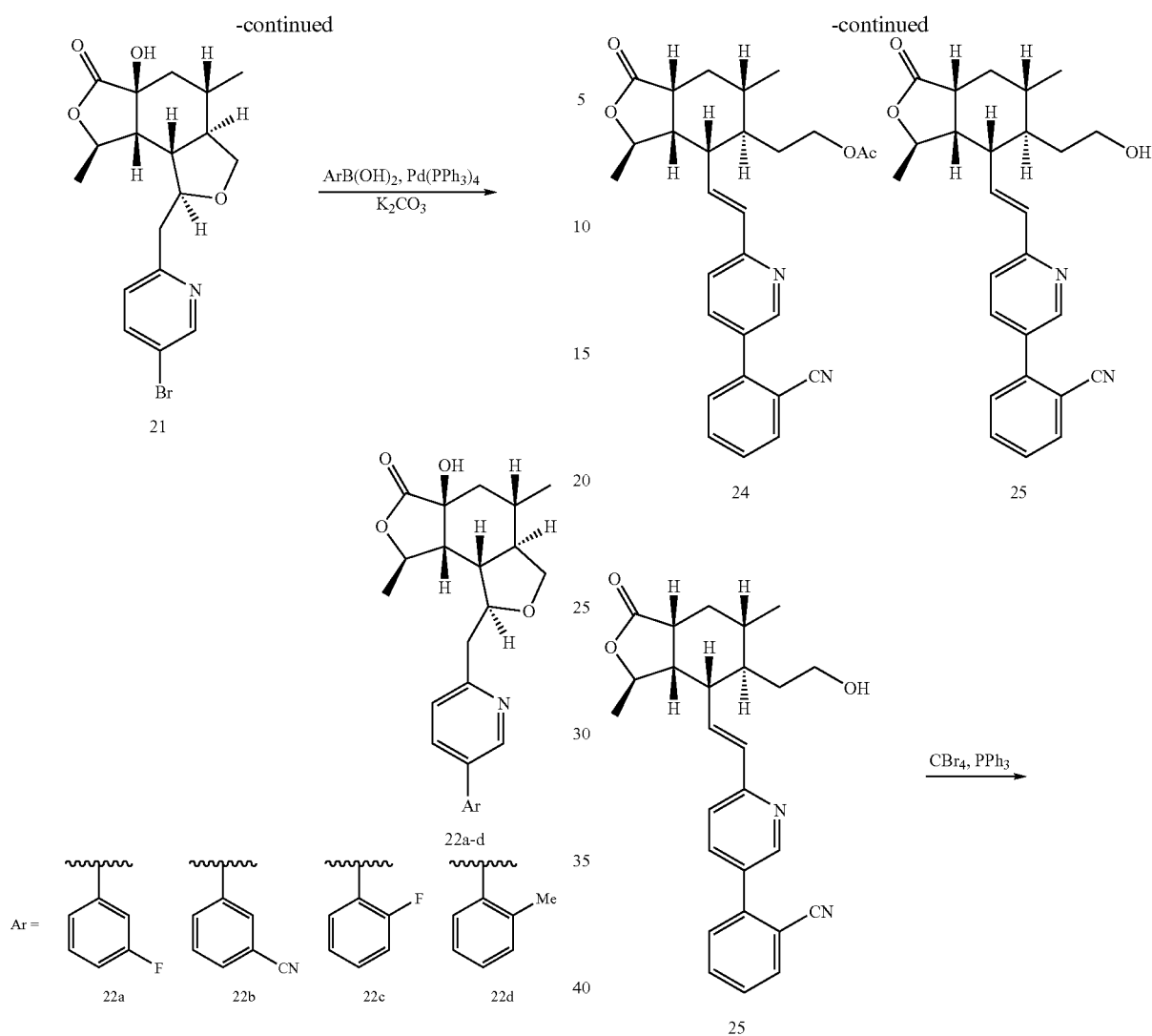
In Scheme 4, Aldehyde 17b was similarly coupled with phosphonate 23, to give a mixture of acetate 24 and alcohol 25. When the alcohol 25 was treated with carbon tetrabromide and triphenyl phosphine, it gave a mixture of bromide 26 and cyclic ether 27. The bromide 26 can be subjected to free radical conditions to provide 28.
Scheme 4
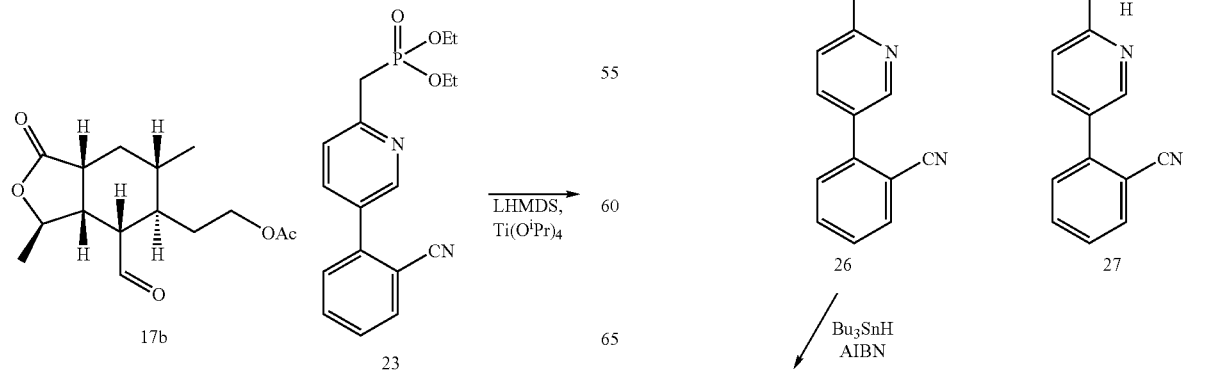

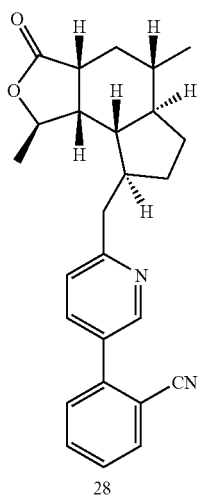

The schematic pathways presented above are rendered in greater detail in the following steps.

Step 1:

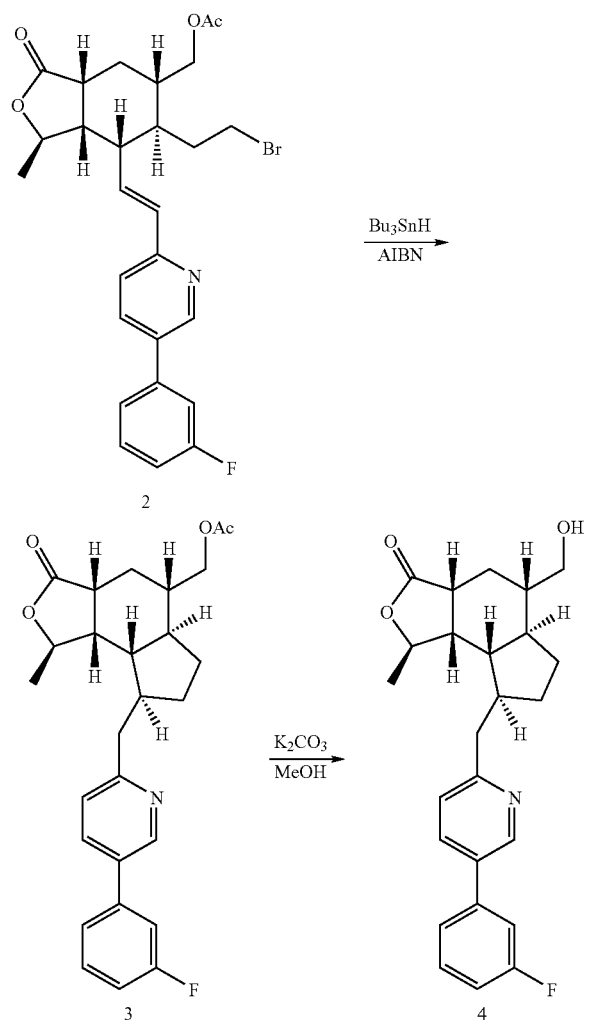

To a solution of 2 (110 mg, 0.207 mmol) (see U.S. Pat. No. 6,645,987 for the preparation of 2) in 6 ml toluene was added AIBN (7 mg, 0.04 mmol, 0.2 eq.) followed by Bu$_3$SnH (170 µl, 0.631 mmol, 3 eq.) and the mixture was heated at reflux for 3 hr. The solution was cooled, concentrated and purified by preparative TLC to provide 69 mg of 3.

To a solution 3 (50 mg, 0.111 mmol) in 2 ml of MeOH—H$_2$O mixture (8:2 v/v) was added K$_2$CO$_3$ (77 mg, 0.557 mmol, 5 eq.) and stirred at rt for 1 hr. The mixture was diluted with aq. NH$_4$Cl and extracted 3 times with CH$_2$Cl$_2$. The combined organic layer was washed with brine, dried over MgSO$_4$, filtered, concentrated and purified by preparative TLC to provide 28 mg of 4. HRMS: 410.2134 (MH$^+$).

Step 2:

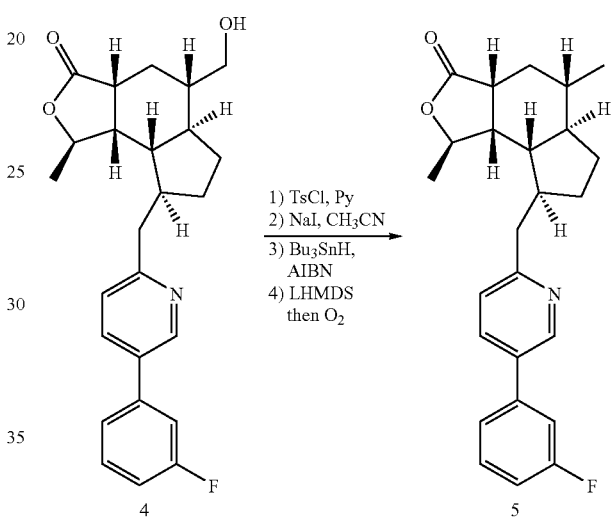

A solution of 4 (130 mg, 0.32 mmol) in 4 ml pyridine at 0° C. was stirred with 5 eq. of TsCl at rt until the reaction was done as indicated by TLC. The pyridine was concentrated and to the residue was added aq. NaHCO$_3$. The mixture was extracted with EtOAc and the crude product was purified by chromatography to provide 135 mg of tosylate.

A solution of the tosylate (135 mg, 0.24 mmol) in 4 ml CH$_3$CN was refluxed overnight with NaI (360 mg, 2.4 mmol, 10 equiv.). The mixture was diluted with 30 ml EtOAc and washed with H$_2$O and brine. It was dried over MgSO$_4$, filtered and concentrated to provide 120 mg of the iodide.

A solution of this iodide (120 mg, 0.23 mmol) in 5 ml benzene was refluxed with 6 eq. of Bu$_3$SnH and 0.4 eq. of AIBN for 3 hr. It was cooled, concentrated and purified by chromatography to provide 80 mg of deiodinated product.

To a solution of this compound (80 mg, 0.203 mmol) in 3 ml THF at 0° C. was added 1M solution of LHMDS in THF (305 µl, 0.305 mmol, 1.5 eq.). After 20 min. of stirring, the flask was evacuated and filled with oxygen and stirred for 1.5 hr then aq. NaHSO$_3$ was added to this. The THF was concentrated, and the aqueous phase was extracted EtOAc. The extracts were dried over MgSO$_4$, filtered, concentrated and purified by preparative TLC to provide 60 mg of 5. MS: 410.1 (MH$^+$).

Step 3:

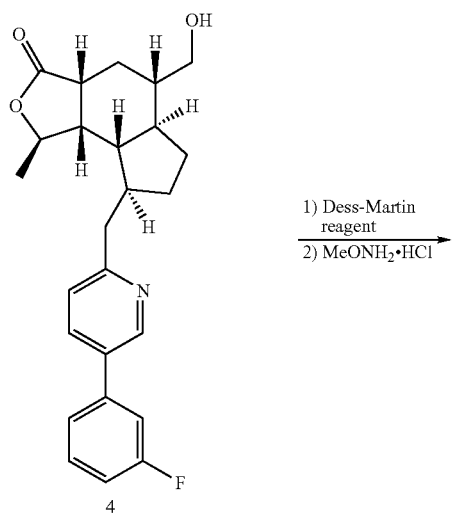

1) Dess-Martin reagent
2) MeONH$_2$·HCl

To a solution of 4 (32 mg, 0.073 mmol) in 2 ml CH$_2$Cl$_2$ was added NaHCO$_3$ (13 mg, 0.155 mmol, 2 eq.) and Dess-Martin periodinane (38 mg, 0.09 mmol, 1.2 eq.). The mixture was stirred at rt for 1.5 hr, diluted with Et$_2$O and stirred with aq. Na$_2$S$_2$O$_3$ until the two layers became clear. The organic layer was separated and the aqueous layer was extracted twice with Et$_2$O. The combined organic layer was washed with brine, dried over MgSO$_4$, filtered and concentrated to provide 30 mg of aldehyde.

The solution of this aldehyde (30 mg, 0.074 mmol) in 0.75 ml pyridine was added hydroxylamine hydrochloride (20 mg, 0.240 mmol) and stirred overnight at rt. The mixture was poured into aq. NH$_4$Cl and extracted with EtOAc. The extract was washed with brine, dried over MgSO$_4$ and purified by chromatography to provide 26 mg of 6. HRMS: 437.2259 (MH$^+$).

Step 4:

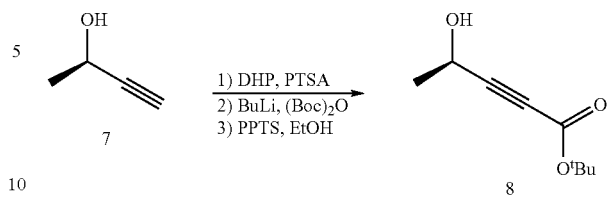

1) DHP, PTSA
2) BuLi, (Boc)$_2$O
3) PPTS, EtOH

To a solution of 7 (10 ml, 127.5 mmol) in neat DHP (12.8 ml, 140.3 mmol, 1.1 eq.) at 0° C. was added p-toluenesulfonic acid monohydrate (243 mg, 1.28 mmol, 1 mol %) and the ice-bath was removed. The mixture was stirred at rt for 2 hr, diluted with THF (200 ml) cooled to −78° C. and a 2.5M solution of BuLi in hexanes (56.1 ml, 140.3 mmol, 1.1 eq.) was added. It was stirred for 1 hr, and a solution of (Boc)$_2$O (34.4 g, 1.2 equiv) in 30 ml THF was added. The mixture was stirred for 1 hr at −78° C., 30 min. at 0° C. then quenched with the addition of 400 ml of aq. NH$_4$Cl. The THF was concentrated and the aqueous slurry was extracted with Et$_2$O (3×150 ml), the combined organic layer was washed with brine, dried over MgSO$_4$, filtered and concentrated to provide 38 g of oil.

This crude product was dissolved in 500 ml of EtOH, 3.2 g of PPTS was added and the solution was heated at 55° C. for 2 hr. The reaction mixture was diluted with 400 ml of aq. NaHCO$_3$, the EtOH was evaporated and the aqueous slurry was extracted with 4×100 ml Et$_2$O. The combined organic layer was washed with brine, dried over MgSO$_4$, filtered concentrated and purified by chromatography to provide 20 g of 8 as oil. $^1$H NMR (400 MHz, CDCl$_3$) 4.61 (q, J=6.8 Hz, 1H), 1.50 (d, J=6.8 Hz, 3H), 1.50 (s, 9H).

Step 5:

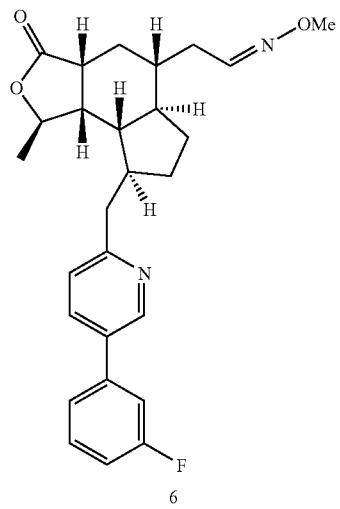

Benzene
reflux

A mixture of known aldehyde 10 (21 g, 128 mmol), (see: Barnett et. al. *Tetrahedron Lett.*, 2001, 57(6), 9741-9746 for the preparation of aldehyde) and the commercially available 9 (41 g, 129 mmol, 1 eq.) in 400 ml benzene was heated in a sealed tube (bath temp. ~85° C.) for about 14 hr. The solution was concentrated and purified by chromatography to provide 16.4 g of 11 as oil. $^1$H NMR (400 MHz, CDCl$_3$) 9.42 (s, 1H), 7.38-7.30 (m, 5H), 6.56 (tq, J=7.0, 1.4, 1H), 4.54 (s, 2H), 3.63 (t, J=6.4, 3H), 2.66 (qd, J=6.6, 0.8, 2H), 1.77-1.76 (m, 3H).

Step 6:

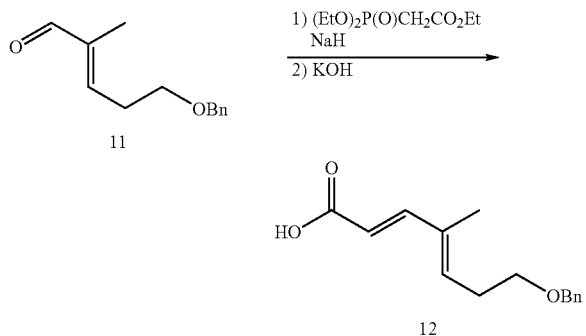

To a suspension of 60% NaH (4.7 g, 118 mmol) in 300 ml THF at rt was added triethylphosphono acetate (24 ml, 121 mmol) and the mixture was stirred at rt for 20 min. To this was added neat 11 (16 g, 78 mmol) and mixture was stirred for 30 min. at rt then quenched by the addition of 400 ml $H_2O$. The THF was evaporated and the aqueous slurry was extracted with 3×150 ml $Et_2O$. The combined organic layer was washed twice with $H_2O$ and once with brine, dried over $MgSO_4$, filtered and concentrated to provide about 24 g of crude product.

This product was dissolved in 100 ml each of THF and MeOH and to this was added a solution of KOH (13.2 g, 235 mmol, 3 eq.) in 100 ml $H_2O$ and the mixture was stirred at rt for 3 hr. The solution was diluted with 500 ml $H_2O$ and washed with 200 ml hexanes after which it was acidified with 1N HCl to ~pH2 and then extracted with 3×150 ml EtOAc. The combined organic layers was washed with $H_2O$ followed by brine, dried over $MgSO_4$, filtered and concentrated to provide 18.6 g of 12 as oil. $^1$H NMR (400 MHz, $CDCl_3$) 7.39-7.23 (m, 6H), 5.95 (t, J=7.2, 1H), 5.77 (d, J=15.6, 1H), 4.48 (s, 2H), 3.51 (t, J=6.8, 2H), 2.50 (q, J=6.8, 2H), 1.76 (d, J=1.2, 3H).

Step 7:

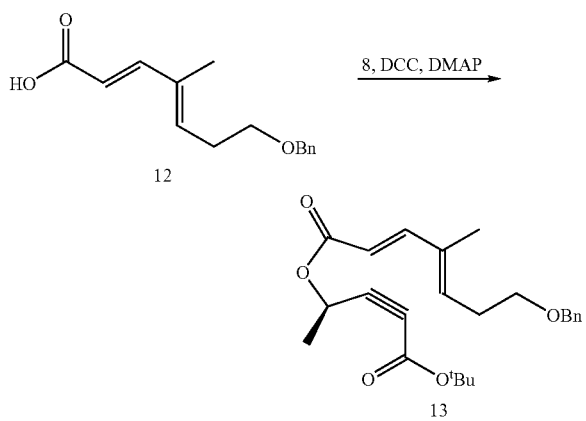

To a solution of 8 (11.7 g, 69 mmol) and 12 (18.6 g, 76 mmol, 1.1 eq.) in 300 ml $CH_2Cl_2$ at 0° C. was added DCC (15.6 g, 76 mmol, 1.1 eq.) and after 10 min. of stirring DMAP (0.84 g, 6.9 mmol, 0.1 eq.) was added and the stirring continued for another 1.5 hr. The reaction mixture was diluted with 500 ml $Et_2O$ and filtered through a celite pad to remove the precipitate. The filtrate was washed with 2×300 ml 1N HCl, 300 ml aq. $NaHCO_3$, and 300 ml brine, dried over $MgSO_4$, filtered, concentrated and chromatographed with 10% EtOAc-hexanes to provide 22 g of 13 as oil. $^1$H NMR (400 MHz, $CDCl_3$) 7.34-7.23 (m, 6H), 5.93 (t, J=7.0, 1H), 5.76 (d, J=15.6, 1H), 5.58 (q, J=6.8, 1H), 4.47 (s, 2H), 3.50 (t, J=6.6, 2H), 2.49 (q, J=6.8, 2H), 1.74 (d, J=1.2, 3H), 1.52 (d, J=6.8, 3H), 1.45 (s, 9H).

Step 8:

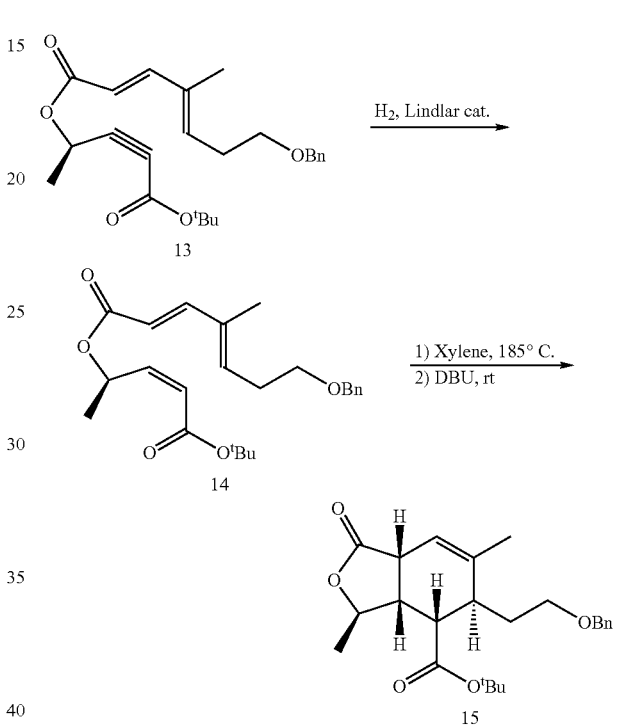

To a solution of 13 (22 g, 55.2 mmol) and quinoline (1.5 g, 11.6 mmol, 0.2 eq.) in 250 ml EtOAc was added Lindlar catalyst (2.2 g, 10 wt %) and the suspension was stirred under a $H_2$ balloon and the reaction was monitored by $^1$H NMR. After about 3.5 hr of stirring the catalyst was removed by filtering through a pad of celite. The organic phase was washed 3 times with 1N HCl followed by brine, dried over $MgSO_4$, filtered and concentrated to provide ~25 g of 14.

This product was dissolved in about 400 ml toluene and heated in a sealed tube for 6 hr (bath temp ~185° C.) then cooled to rt, concentrated and chromatographed with 15% EtOAc-hexanes to provide 7.2 g of exo adduct. The exo product was dissolved in 100 ml $CH_2Cl_2$ and stirred with DBU (540 µl, 3.91 mmol, 0.2 eq.) for 45 min. then diluted with 100 ml $Et_2O$ and washed with 3×50 ml 1N HCl followed by brine. It was dried over $MgSO_4$, filtered and concentrated to provide 7.0 g of 15. $^1$H NMR (400 MHz, $CDCl_3$) 7.31-7.21 (m, 5H), 5.45-5.43 (m, 1H), 4.53-4.47 (m, 1H), 4.43 (dd, J=12.0, 14.8, 2H), 3.41 (td, J=6.4, 1.2, 2H), 3.16-3.12 (m, 1H), 2.78 (dd, J=7.6, 4.8, 1H), 2.56-2.51 (m, 1H), 2.46-2.45 (m, 1H), 1.86-1.70 (m, 2H), 1.70 (s, 3H), 1.37 (s, 9H), 1.29 (d, J=6.4, 3H).

Step 9:

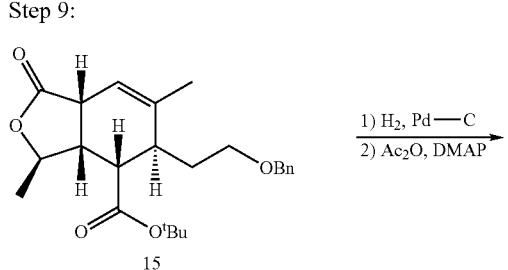

To a solution of 15 (7 g) in 50 ml MeOH was added 10% Pd-C (700 mg) and suspension was shaken overnight under 50 psi $H_2$ in a parr vessel. The catalyst was filtered off and the product was purified by chromatography followed by recrystallization from TBME-hexanes to provide a combined yield of 3.26 g of alcohol.

To a solution of this alcohol (1.1 g, 3.52 mmol) and DMAP (43 mg, 0.35 mmol, 0.1 eq.) in 20 ml $CH_2Cl_2$ at 0° C. was added $Ac_2O$ (500 μl, 5.29 mmol, 1.5 eq.) followed by $Et_3N$ (980 μl, 7.03 mmol, 2 eq.). The solution was stirred for 2 hr, diluted with 100 ml $Et_2O$ and washed twice with aq. $NaHCO_3$ and once with brine, dried over $MgSO_4$, filtered, concentrated and chromatographed with 20% EtOAc-hex to provide 1.16 g of 16. $^1$H NMR (400 MHz, $CDCl_3$) 4.69 (dq, J=9.8, 5.8, 1H), 4.11-4.00 (m, 2H), 2.60-2.52 (m, 2H), 2.45-2.39 (m, 1H), 2.00 (s, 3H), 1.91 (ddd, J=13.4, 6.0, 2.6, 1H), 1.72-1.67 (m, 2H), 1.54-1.38 (m, 2H), 1.43 (s, 9H), 1.31 (d, J=6.0, 3H), 1.24-1.18 (m, 1H), 0.99 (d, J=6.4, 3H).

Step 10:

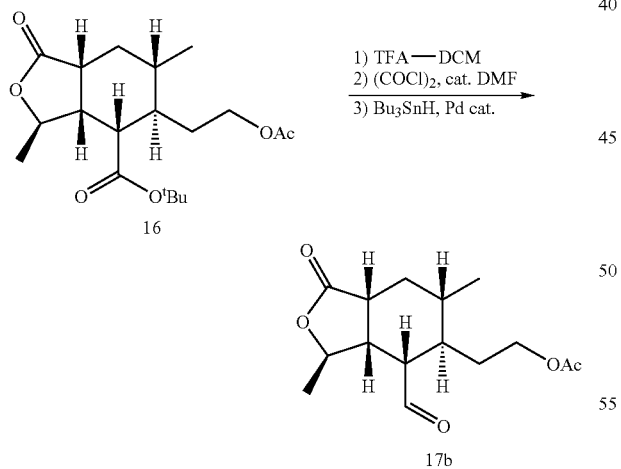

To a solution 16 (1.15 g, 3.25 mmol) in 10 ml $CH_2Cl_2$ was added 10 ml TFA. The mixture was stirred for 1 hr at rt, concentrated and evaporated with toluene to provide the acid.

The acid was dissolved in 20 ml $CH_2Cl_2$ and stirred with oxalylchloride (570 μl, 6.53 mmol, 2 eq.) and 2 drops of DMF. After stirring for 1 hr, the solution was concentrated and evaporated with toluene to provide the acid chloride.

To a solution of this acid chloride in 20 ml toluene at rt was added $Pd(PPh_3)_4$ followed by $Bu_3SnH$ (1.8 ml, 6.69 mmol, 2 eq.). The mixture was stirred for 30 min. then concentrated and chromatographed with 40% EtOAc-hex to provide 760 mg of 17b. $^1$H NMR (400 MHz, $CDCl_3$) 9.73 (d, J=2.4, 1H), 4.62 (dq, J=9.6, 6.0, 1H), 4.10-4.00 (m, 2H), 2.73 (ddd, J=10.8, 5.6, 2.4, 1H), 2.70-2.63 (m, 1H), 2.59-2.53 (m, 1H), 1.99 (s, 3H), 1.96 (ddd, J=13.8, 6.4, 3.0, 1H), 1.77-1.60 (m, 3H), 1.38-1.32 (m, 1H), 1.30 (d, J=6.4, 3H), 1.24-1.14 (m, 1H), 1.02 (d, J=6.4, 3H).

Step 11:

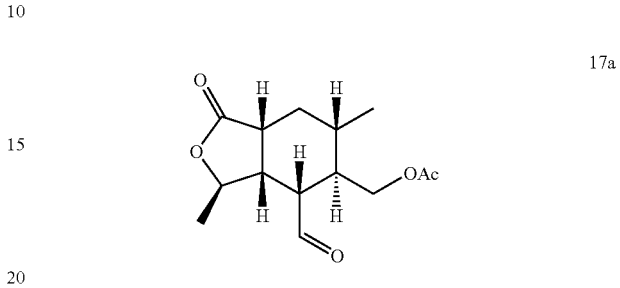

Aldehyde 17a was prepared using a procedure similar to the preparation of aldehyde 17b. $^1$H NMR (400 MHz, $CDCl_3$) 9.76 (d, J=2.4, 1H), 4.61 (dq, J=9.6, 6.0, 1H), 4.25 (dd, J=11.6, 2.8, 1H), 4.14 (dd, J=12.0, 4.8, 1H), 2.84 (ddd, J=10.8, 5.6, 2.4, 1H), 2.75-2.68 (m, 1H), 2.66-2.61 (m, 1H), 2.04 (s, 3H), 2.04-1.98 (m, 1H), 1.93-1.85 (m, 1H), 1.52-1.42 (m, 1H), 1.35 (d, J=6.0, 3H), 1.40-1.26 (m, 1H), 1.07 (d, J=6.4, 3H).

Step 12:

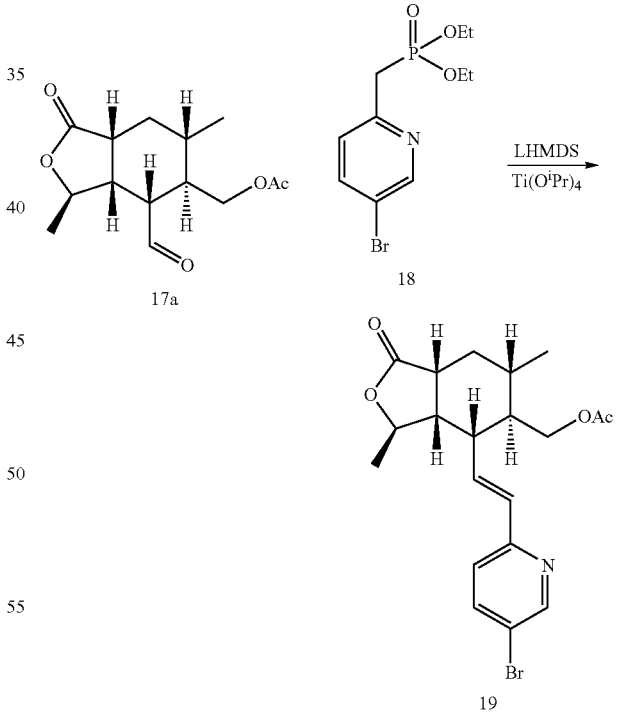

To a solution of phosphonate 18 (720 mg, 2.34 mmol, 2 eq.) in 5 ml THF at 0° C. was added a solution of 1M LHMDS in THF (2.3 ml, 2.3 mmol, 2 eq.) and the mixture was stirred for 20 min. (See U.S. Pat. No. 6,645,987 for the preparation of 18.) To this was added $Ti(O^iPr)_4$ followed by a solution of 17a (330 mg, 1.16 mmol) in 3 ml THF. The ice-bath was removed and the solution was stirred at rt for 45 min. then quenched by the addition of ~70 ml aq. Na-K-tartrate. The THF was evaporated and the aqueous phase was extracted with 3×30 ml EtOAc, the combined organic layer was washed with brine, dried over MgSO$_4$, filtered, concentrated and chromatographed with 30% EtOAc-hex to provide 460 mg of 19. $^1$H NMR (400 MHz, CDCl$_3$) 8.58 (d, J=2.4, 1H), 7.75 (dd, J=8.0, 2.4, 1H), 7.07 (d, J=8.4, 1H), 6.59 (dd, J=15.6, 10.2, 1H), 6.43 (d, J=15.6, 1H), 4.74-4.67 (m, 1H), 4.29 (dd, J=11.6, 3.2, 1H), 4.01 (dd, J=11.6, 2.4, 1H), 2.78-2.67 (m, 2H), 2.38 (dt, J=10.0, 6.5, 1H), 2.05-2.00 (m, 1H), 2.02 (s, 3H), 1.61-1.55 (m, 1H), 1.47-1.38 (m, 1H), 1.40 (d, J=6.0, 3H), 1.38-1.25 (m, 1H), 1.04 (d, J=6.4, 3H).

Step 13:

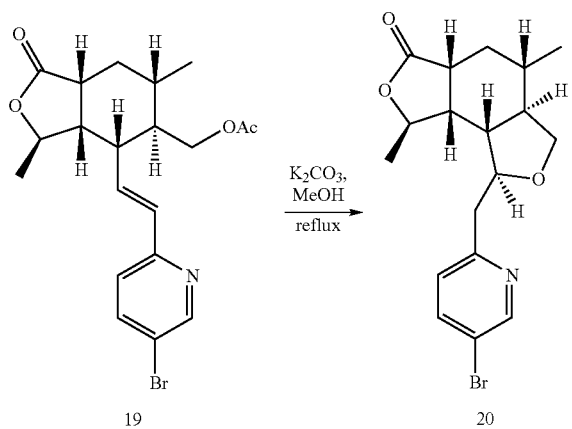

A mixture of 19 (570 mg, 1.35 mmol) and K$_2$CO$_3$ (750 mg, 5.43 mmol, 4 eq.) in 10 ml MeOH was heated at reflux for 5 hr. The MeOH was concentrated and the mixture stirred with aq. NH$_4$Cl and extracted with 4×30 ml EtOAc. The combined organic layer was washed with brine, dried over MgSO$_4$, filtered, concentrated and chromatographed with 35% EtOAc-hex to provide 440 mg of 20. $^1$H NMR (400 MHz, CDCl$_3$) 8.59 (d, J=2.4, 1H), 7.73 (dd, J=8.4, 2.6, 1H), 7.17 (d, J=8.4, 1H), 4.60-4.52 (m, 1H), 4.07-4.02 (m, 2H), 3.39 (dd, J=10.2, 8.2, 1H), 3.12 (dd, J=14.0, 3.2, 1H), 2.85 (dd, J=14.0, 7.6, 1H), 2.70 (dt, J=12.8, 6.8, 1H), 2.52-2.46 (m, 1H), 2.07 (ddd, J=14.0, 6.8, 3.2, 1H), 1.71-1.67 (m, 2H), 1.44 (dd, J=6.0, 3H), 1.41-1.25 (m, 1H), 1.19-1.09 (m, 1H), 0.94 (d, J=6.4, 3H).

Step 14:

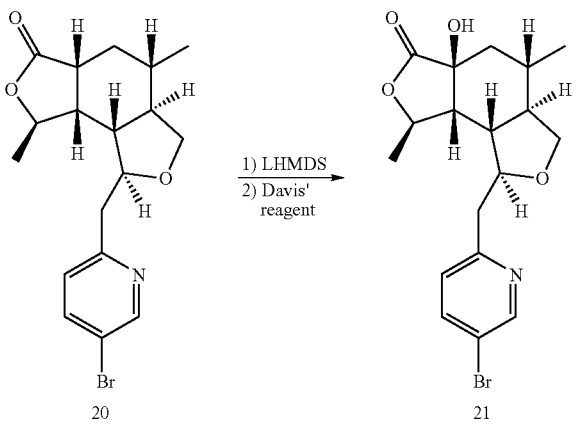

To a solution of 20 (310 mg, 0.815 mmol) in 5 ml THF at −78° C. was added a solution of 1M LHMDS in THF (0.98 ml, 0.98 mmol, 1.2 eq.) and stirred for 15 min. at −78° C., 15 min at 0° C. and cooled back to −78° C. To this was added a solution of (1S)-(+)-(10-camphorsulfonyl)oxaziridine (280 mg, 1.22 mmol, 1.5 eq.) in 2.5 ml THF and the mixture was stirred for 30 min. then allowed to warm to rt slowly. It was quenched by the addition of 100 ml aq. NH$_4$Cl and the THF was evaporated. The aqueous phase was extracted with 3×25 ml EtOAc and the combined organic layer was washed with brine, dried over MgSO$_4$, filtered, concentrated and chromatographed to provide 150 mg of 21. $^1$H NMR (400 MHz, CDCl$_3$) 8.59 (d, J=2.4, 1H), 7.73 (dd, J=8.4, 2.4, 1H), 7.17 (d. J=8.4, 1H), 4.49-4.42 (m, 1H), 4.12-4.02 (m, 2H), 3.45 (dd, J=9.6, 8.0, 1H), 3.17 (br s, 1H), 3.10 (dd, J=14.0, 3.2, 1H), 2.88 (dd, J=14.0, 7.8, 1H), 2.42 (dd, J=9.6, 5.2, 1H), 1.93 (td, J=11.6, 5.2, 1H), 1.85 (d, J=7.0, 1H), 1.74-1.69 (m, 2H), 1.45 (d, J=6.0, 3H), 1.32 (dd, J=14.2, 11.4, 1H), 0.93 (d, J=6.0, 3H).

Step 15:

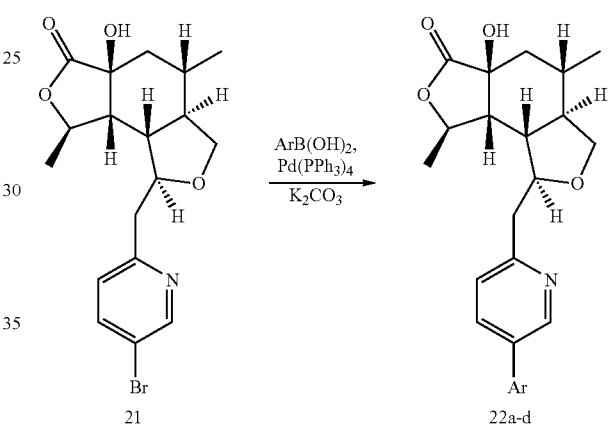

A mixture of 21, Pd(PPh$_3$)$_4$ (5 mol %), K$_2$CO$_3$ (4 eq.) and the appropriate boronic acid (1.5 eq.) in PhMe-EtOH-H$_2$O (4:2:1 v/v/v) was heated at 100° C. for 5 hr, diluted with H$_2$O, and extracted with EtOAc. The organic layer was washed with brine, dried over MgSO$_4$, filtered, evaporated and purified by preparative TLC to provide analogs 22a-d (as shown in Scheme 3 above). MS for 22a: m/e 412.1 (MH$^+$). MS for 22b: m/e 419.1 (MH$^+$). MS for 22c: m/e 412.1 (MH$^+$). MS for 22d: m/e 408.1 (MH$^+$).

Step 16:

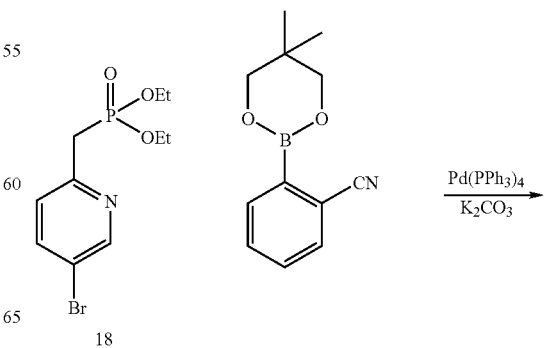

-continued

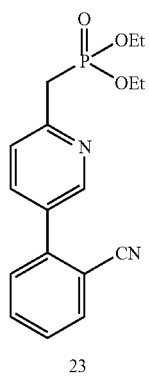

23

A solution of 18 (2.12 g, 6.88 mmol), Pd(PPh$_3$)$_4$ (400 mg, 0.346 mmol, 5 mol %), (2-cyanophenyl)boronic acid 2,2-dimethylpropanediol-1,3-cyclic ester (1.8 g, 8.37 mmol, 1.2 eq.) and K$_2$CO$_3$ (3.0 g, 27.49 mmol, 4 eq.) in toluene(20 ml)-EtOH(10 ml)-H$_2$O(5 ml) mixture was heated in a sealed tube at 100° C. for 4 hr. The mixture was diluted with 150 ml H$_2$O and extracted with 3×50 ml EtOAc. The combined organic layer was washed with brine, dried over MgSO$_4$, filtered, concentrated and purified by chromatography to provide 23 (1.82 g) as a solid. $^1$H NMR (400 MHz, CDCl$_3$) 8.66 (d, J=2.0, 1H), 7.86 (dd, J=8.0, 2.0, 1H), 7.78-7.75 (m, 1H), 7.68-7.64 (m, 1H), 7.50-7.45 (m, 3H), 4.08 (dq, J=8.0, 7.2, 4H), 3.46 (d, J=22, 2H), 1.26 (t, 6H).

Step 17:

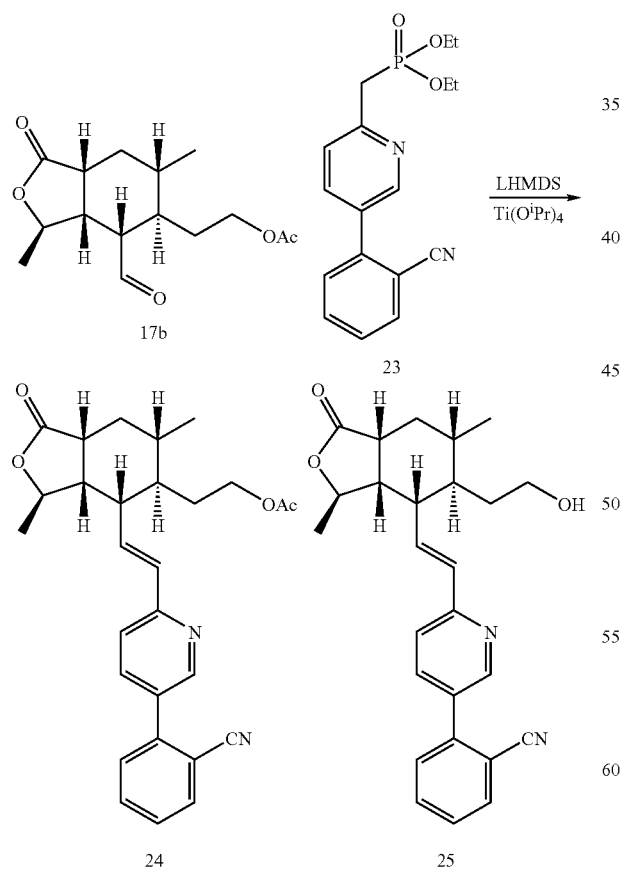

To a solution of phosphonate 23 (1.33 g, 4.03 mmol) in 15 ml THF at 0° C. was added a solution of 1M LHMDS in THF and the mixture was stirred for 15 min. To this was added Ti(O$^i$Pr)$_4$ followed by a solution of 17b in 5 ml THF and the mixture was stirred overnight (0° C. to rt). The reaction mixture was diluted with 100 ml of aq. Na-K-tartrate and the THF was evaporated. The slurry was extracted with 3×30 ml of EtOAc and the combined organic layer was washed with brine, dried over MgSO$_4$, filtered, evaporated and chromatographed with 50% EtOAc-hex to 100% EtOAc to provide 420 mg of 24 and 510 mg of 25. MS for 24: m/e 459.1 (MH$^+$). MS for 25: m/e 417.1 (MH$^+$).

Step 18:

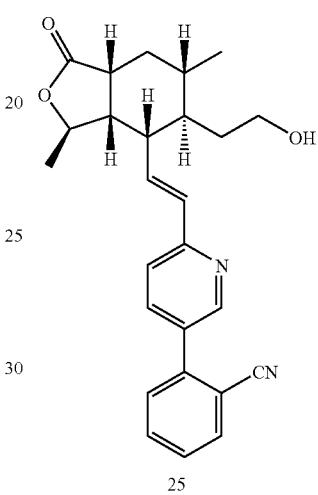

25

CBr$_4$, PPh$_3$ →

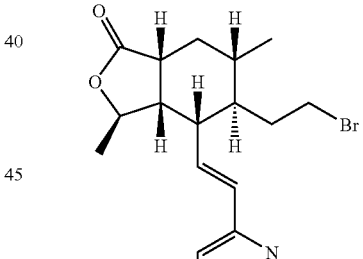

26

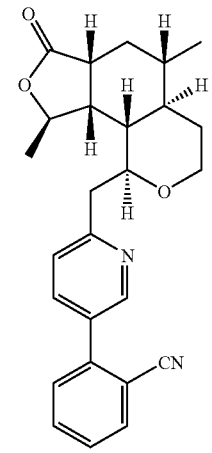

27

To a solution of 25 (105 mg, 0.230 mmol) and CBr$_4$ (155 mg, 0.467 mmol, 2 eq.) in 2.5 ml THF at 0° C. was added PPh$_3$ and the ice-bath was removed. After stirring overnight the mixture was concentrated and purified by silica gel chromatography to provide 26 (52 mg) and 27 (19 mg). MS for 26: m/e 481.3 (MH$^+$). MS for 27: m/e 417.2 (MH$^+$).

Step 19:

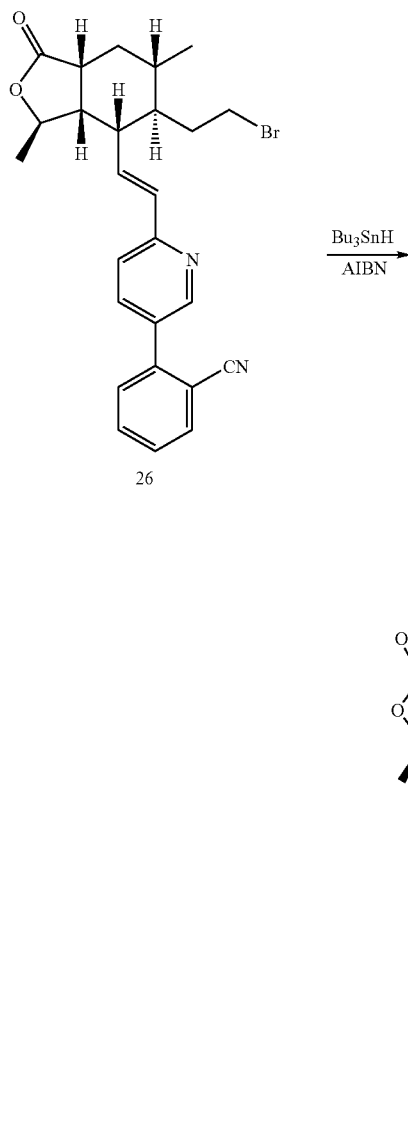

A solution of 26 (51 mg, 0.106 mmol), Bu$_3$SnH (58 µl, 0.215 mmol, 2 eq.) and AIBN (1.8 mg, 0.011 mmol, 0.1 eq.) in 2 ml benzene was heated at reflux for 2 hr, cooled to rt, concentrated and chromatographed with 50% EtOAc-hex to provide 35 mg of 28. MS: m/e 401.2 (MH$^+$).

Starting materials for the above processes are either commercially available, known in the art, or prepared by procedures well known in the art.

Reactive groups not involved in the above processes can be protected during the reactions with conventional protecting groups which can be removed by standard procedures after the reaction. The following Table A shows some typical protecting groups:

TABLE A

| Group to be Protected | Group to be Protected and Protecting Group |
|---|---|
| —COOH | —COOalkyl, —COObenzyl, —COOphenyl |
| \NH/ | \NCOalkyl/, \NCObenzyl/, \NCOphenyl/, \NCH$_2$OCH$_2$CH$_2$Si(CH$_3$)$_3$/, \NC(O)OC(CH$_3$)$_3$/, \N-benzyl/, \NSi(CH$_3$)$_3$/, \NSi(CH$_3$)$_2$—C(CH$_3$)$_3$/ |
| —NH$_2$ | succinimide |
| —OH | —OCH$_3$, —OCH$_2$OCH$_3$, —OSi(CH$_3$)$_3$, —OSi(CH$_3$)$_2$—C(CH$_3$)$_3$ or —OCH$_2$phenyl |

The present invention also relates to pharmaceutical compositions comprising at least one compound of Formula I of this invention and a pharmaceutically acceptable carrier. The compounds of Formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily dose of a compound of Formula I for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2-4 divided doses. The exact dose, however, is determined by the attending clinician and is dependent on the potency of the compound administered, the age, weight, condition and response of the patient.

The following formulations exemplify some of the dosage forms of this invention. In each, the term "active compound" designates a compound of Formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

Method of Manufacture

Mix Item Nos. 1 and 2 in suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|   | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

Methods of Treatment and Co-Formulations

U.S. application Ser. No. 10/705,282 discloses a number of methods of treatment and co-formulations regarding other families of thrombin receptor antagonists. Similarly, with respect to the present invention, further embodiments encompass the administration of at least one compound of Formula I along with at least one additional therapeutically effective agent. The contemplated additional therapeutically effective agent is one that differs in either atomic make up or arrangement from the compounds of Formula I. Therapeutically effective agents that can be used in combination with the novel compounds of this invention include drugs that are known and used in the treatment of inflammation, rheumatism, asthma, glomerulonephritis, osteoporosis, neuropathy and/or malignant tumors, angiogenesis related disorders, cancer, disorders of the liver, kidney and lung, melanoma, renal cell carcinoma, renal disease, acute renal failure, chronic renal failure, renal vascular homeostasis, glomerulonephritis, chronic airways disease, bladder inflammation, neurodegenerative and/or neurotoxic diseases, conditions, or injuries, radiation fibrosis, endothelial dysfunction, periodontal diseases and wounds. Further examples of therapeutically effective agents which may be administered in combination with the compounds of Formula I include resistance factors for tumor cells towards chemotherapy and proliferation inhibitors of smooth muscle cells, endothelial cells, fibroblasts, kidney cells, osteosarcoma cells, muscle cells, cancer cells and/or glial cells. The therapeutically effective agents may be cardiovascular agents.

Cardiovascular agents that can be used in combination with the novel compounds of this invention include drugs that have anti-thrombotic, anti-platelet aggregation, antiatherosclerotic, antirestenotic and/or anti-coagulant activity. Such drugs are useful in treating thrombosis-related diseases including thrombosis, atherosclerosis, restenosis, hypertension, angina pectoris, arrhythmia, heart failure, myocardial infarction, glomerulonephritis, thrombotic and thromboembolic stroke, peripheral vascular diseases, other cardiovascular diseases, cerebral ischemia, inflammatory disorders and cancer, as well as other disorders in which thrombin and its receptor play a pathological role. Suitable cardiovascular agents are selected from the group consisting of thromboxane $A_2$ biosynthesis inhibitors such as aspirin; thromboxane antagonists such as seratrodast, picotamide and ramatroban; adenosine diphosphate (ADP) inhibitors such as clopidogrel; cyclooxygenase inhibitors such as aspirin, meloxicam, rofecoxib and celecoxib; angiotensin antagonists such as valsartan, telmisartan, candesartan, irbesartran, losartan and eprosartan; endothelin antagonists such as tezosentan; phosphodiesterase inhibitors such as milrinoone and enoximone; angiotensin converting enzyme (ACE) inhibitors such as captopril, enalapril, enaliprilat, spirapril, quinapril, perindopril, ramipril, fosinopril, trandolapril, lisinopril, moexipril and benazapril; neutral endopeptidase inhibitors such as candoxatril and ecadotril; anticoagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists.

Preferred types of drugs for use in combination with the novel compounds of this invention are thromboxane $A_2$ biosynthesis inhibitors, cyclooxygenase inhibitors and ADP antagonists. Especially preferred for use in the combinations are aspirin and clopidogrel bisulfate.

Further embodiments of the invention encompass the administration of at least one compound of Formula I along with more than one additional therapeutically effective agent. In these embodiments, the additional therapeutically effective agent may or may not be commonly used in the treatment of the same condition. For example, a compound of Formula I may be administered along with two cardiovascular agents. Alternatively, a compound of Formula I may be administered along with a cardiovascular agent and a therapeutically effective agent useful in the treatment of inflammation.

When the invention comprises a combination of at least one compound of Formula I and one or more other therapeutically effective agents, the two or more active components may be co-administered simultaneously or sequentially, or a single pharmaceutical composition comprising the at least one compound of Formula I and the other therapeutically effective agent(s) in a pharmaceutically acceptable carrier can be administered. The components of the combination can be administered individually or together in any conventional dosage form such as capsule, tablet, powder, cachet, suspension, solution, suppository, nasal spray, etc. The dosage of the other therapeutically active agent(s) can be determined from published material, and may range from 1 to 1000 mg per dose.

In this specification, the term "at least one compound of Formula I" means that one to three different compounds of Formula I may be used in a pharmaceutical composition or method of treatment. Preferably one compound of Formula I is used. Similarly, the term "one or more additional cardiovascular agents" means that one to three additional drugs may be administered in combination with a compound of Formula I; preferably, one additional compound is administered in combination with a compound of Formula I. The additional cardiovascular agents can be administered sequentially or simultaneously with reference to the compound of Formula I.

In Vitro Testing Procedure for Thrombin Receptor Antagonists:

The activity of the compounds of Formula I can be determined by the following procedures.

Preparation of [$^3$H]haTRAP

A(pF-F)R(ChA)(hR)(I$_2$-Y)-NH$_2$ (1.03 mg) and 10% Pd/C (5.07 mg) were suspended in DMF (250 µl) and diisopropylethylamine (10 µl). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H]haTRAP) was dissolved in 0.5 ml of 0.1% aqueous TFA and purified by HPLC using the following conditions: column, Vydac C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al (Natarajan et al, *Int. J. Peptide Protein Res.* 45:145-151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were resuspended in 10 mM Tris-HCl, pH 7.5, 150 mM NaCl, 5 mM EDTA, to a total volume of 200 ml and centrifuged at 4400×g for 10 minutes. This step was repeated two additional times. Platelets were resuspended in 5 mM Tris-HCl, pH 7.5, 5 mM EDTA to a final volume of approximately 30 ml and were homogenized with 20 strokes in a Dounce homogenizer. Membranes were pelleted at 41,000×g, resuspended in 40-50 ml 20 mM Tris-HCl, pH 7.5, 1 mM EDTA, 0.1 mM dithiothreitol, and 10 ml aliquots were frozen in liquid N$_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and resuspended in 20-25 ml 50 mM Tris-HCl, pH 7.5, 10 mM MgCl$_2$, 1 mM EGTA, and 1% DMSO. Aliquots of membranes were frozen in liquid N$_2$ and stored at −80° C. Membranes were stable for at least 3 months. 20 units of platelet concentrates typically yielded 250 mg of membrane protein. Protein concentration was determined by a Lowry assay (Lowry et al, *J. Biol. Chem.* 193:265-275 (1951)).

High Throughput Thrombin Receptor Radioligand Binding Assay

Thrombin receptor antagonists were screened using a modification of the thrombin receptor radioligand binding assay of Ahn et al. (Ahn et al, *Mol. Pharmacol.*, 51:350-356 (1997)). The assay was performed in 96 well Nunc plates (Cat. No. 269620) at a final assay volume of 200 µl. Platelet membranes and [$^3$H]haTRAP were diluted to 0.4 mg/ml and 22.2 nM, respectively, in binding buffer (50 mM Tris-HCl, pH 7.5, 10 mM MgCl$_2$, 1 mM EGTA, 0.1% BSA). Stock solutions (10 mM in 100% DMSO) of test compounds were further diluted in 100% DMSO. Unless otherwise indicated, 10 µl of diluted compound solutions and 90 µl of radioligand (a final concentration of 10 nM in 5% DMSO) were added to each well, and the reaction was started by the addition of 100 µl of membranes (40 µg protein/well). The binding was not significantly inhibited by 5% DMSO. Compounds were tested at three concentrations (0.1, 1 and 10 µM). The plates were covered and vortex-mixed gently on a Lab-Line Titer Plate Shaker for 1 hour at room temperature. Packard UniFilter GF/C filter plates were soaked for at least 1 hour in 0.1% polyethyleneimine. The incubated membranes were harvested using a Packard FilterMate Universal Harvester and were rapidly washed four times with 300 µl ice cold 50 mM Tris-HCl, pH 7.5, 10 mM MgCl$_2$, 1 mM EGTA. MicroScint 20 scintillation cocktail (25 µl) was added to each well, and the plates were counted in a Packard TopCount Microplate Scintillation Counter. The specific binding was defined as the total binding minus the nonspecific binding observed in the presence of excess (50 µM) unlabeled haTRAP. The % inhibition by a compound of [$^3$H]haTRAP binding to thrombin receptors was calculated from the following relationship:

$$\% \text{ Inhibition} = \frac{\text{Total binding} - \text{Binding in the presence of a test compound}}{\text{Total binding} - \text{Nonspecific binding}} \times 100$$

Materials

A(pF-F)R(ChA)(hR)Y-NH$_2$ and A(pF-F)R(ChA)(hR)(I$_2$-Y)-NH$_2$, were custom synthesized by AnaSpec Inc. (San Jose, Calif.). The purity of these peptides was >95%. Tritium gas (97%) was purchased from EG&G Mound, Miamisburg Ohio. The gas was subsequently loaded and stored on an IN/US Systems Inc. Trisorber. MicroScint 20 scintillation cocktail was obtained from Packard Instrument Co.

Using the test procedures described above, representative compounds of Formula I were found to have thrombin receptor IC$_{50}$ values (i.e., the concentration at which a 50% inhibition of thrombin receptor was observed) of 1 to 1000 nM, preferably 1-100 nM, more preferably 1-20 nM.

We claim:

1. A compound represented by the structural formula

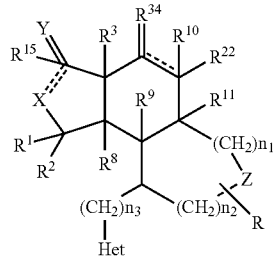

Formula 1 or a pharmaceutically acceptable salt or solvate thereof, wherein:

the single-dashed line

----- between the ring carbons to which R$^{10}$ and R$^{34}$ are attached represents either a single bond or a double bond;

the double-dashed line

===== between X and the carbon to which Y is attached represents a single bond;

X is —O—;

$R^{15}$ is H, or $C_1$-$C_6$ alkyl;

Y is (O), (S), (H, H), (H, OH) or (H, $C_1$-$C_6$ alkoxy);

Z is selected from the group consisting of —CH$_2$— and —O—;

$n_1$ is 1 or 2;

$n_2$ is 0;

$n_3$ is 1;

$n_4$ is 0, 1 or 2;

R is 1 to 3 substituents independently selected from the group consisting of H, $C_1$-$C_6$ alkyl, halogen, hydroxy, amino, ($C_1$-$C_6$) alkyl-amino, ($C_1$-$C_6$)dialkylamino, ($C_1$-$C_6$)alkoxy, —COR$^{16}$, —COOR$^{17}$, —SOR$^{16}$, —SO$_2$R$^{16}$, —NR$^{16}$COR$^{16a}$, —NR$^{16}$COOR$^{16a}$, —NR$^{16}$CONR$^4$R$^5$, fluoro-($C_1$-$C_6$)alkyl, difluoro($C_1$-$C_6$)alkyl, trifluoro($C_1$-$C_6$)alkyl, $C_3$-$C_6$ cycloalkyl, $C_2$-$C_6$ alkenyl, aryl($C_1$-$C_6$)alkyl, aryl($C_2$-$C_6$)alkenyl, heteroaryl($C_1$-$C_6$)-alkyl, heteroaryl($C_2$-$C_6$)alkenyl, hydroxy($C_1$-$C_6$)alkyl, amino($C_1$-$C_6$)-alkyl, aryl and thio($C_1$-$C_6$)alkyl;

$R^1$ and $R^2$ are independently selected from the group consisting of H, $C_1$-$C_6$ alkyl, fluoro($C_1$-$C_6$)alkyl, difluoro($C_1$-$C_6$)alkyl, trifluoro-($C_1$-$C_6$)alkyl, $C_3$-$C_7$ cycloalkyl, $C_2$-$C_6$ alkenyl, aryl($C_1$-$C_6$)alkyl, aryl($C_2$-$C_6$)alkenyl, heteroaryl($C_1$-$C_6$)alkyl, heteroaryl($C_2$-$C_6$)alkenyl, hydroxy-($C_1$-$C_6$)alkyl, ($C_1$-$C_6$)alkoxy($C_1$-$C_6$)alkyl, amino-($C_1$-$C_6$)alkyl, aryl and thio($C_1$-$C_6$)alkyl; or $R^1$ and $R^2$ together form a =O group;

$R^3$ is H, hydroxy, $C_1$-$C_6$ alkoxy, —NR$^{18}$R$^{19}$, —SOR$^{16}$, —SO$_2$R$^{17}$, —C(O)OR$^{17}$, —C(O)NR$^{18}$R$^{19}$, $C_1$-$C_6$ alkyl, halogen, fluoro($C_1$-$C_6$)alkyl, difluoro($C_1$-$C_6$)alkyl, trifluoro($C_1$-$C_6$)alkyl, $C_3$-$C_7$ cycloalkyl, $C_2$-$C_6$ alkenyl, aryl($C_1$-$C_6$)alkyl, aryl($C_2$-$C_6$)alkenyl, heteroaryl($C_1$-$C_6$)alkyl, heteroaryl($C_2$-$C_6$)alkenyl, hydroxy($C_1$-$C_6$)alkyl, amino($C_1$-$C_6$)alkyl, aryl, thio($C_1$-$C_6$)alkyl, ($C_1$-$C_6$)alkoxy($C_1$-$C_6$)alkyl or ($C_1$-$C_6$)alkylamino($C_1$-$C_6$)alkyl, —O-aryl, N$_3$, NO$_2$, C(=NR$^1$)NR$^1$R$^2$, N=C(R$^1$)NR$^1$R$^2$, NR$^{18}$COR$^{19}$, NR$^{18}$CONR$^{18}$R$^{19}$, NR$^{18}$C(O)OR$^{19}$, NR$^{18}$S(O)$_2$R$^{19}$, NR$^{18}$S(O)$_2$NR$^{18}$R$^{19}$, NHNR$^{18}$R$^9$, NR$^{18}$NR$^{18}$R$^{19}$ or NR$^{18}$R$^{19}$; Het is pyridyl, wherein the Het group is optionally substituted by W, wherein W is selected from the group consisting of aryl optionally substituted by halo or CN;

$R^4$ and $R^5$ are independently selected from the group consisting of H, $C_1$-$C_6$ alkyl, phenyl, benzyl and $C_3$-$C_7$ cycloalkyl, or $R^4$ and $R^5$ together are —(CH$_2$)$_4$—, —(CH$_2$)$_5$— or —(CH$_2$)$_2$NR$^7$—(CH$_2$)$_2$— and form a heterocyclyl ring with the nitrogen to which they are attached;

$R^6$ is independently selected from the group consisting of H, $C_1$-$C_6$ alkyl, phenyl, ($C_3$-$C_7$)cycloalkyl, ($C_3$-$C_7$)cycloalkyl($C_1$-$C_6$)alkyl, ($C_1$-$C_6$)alkoxy($C_1$-$C_6$)alkyl, hydroxy($C_1$-$C_6$)alkyl and amino($C_1$-$C_6$)alkyl;

$R^7$ is H or ($C_1$-$C_6$)alkyl;

$R^8$, $R^{10}$ and $R^{11}$ are independently selected from the group consisting of $R^1$ and —OR$^1$, provided that when the single-dashed line is a double bond, $R^{10}$ is absent;

$R^9$ is H, OH, $C_1$-$C_6$ alkoxy, halogen or halo($C_1$-$C_6$)alkyl;

$R^{16}$ and $R^{16a}$ are independently selected from the group consisting of $C_1$-$C_6$ lower alkyl, phenyl or benzyl;

$R^{17}$, $R^{18}$ and $R^{19}$ are independently selected from the group consisting of H, $C_1$-$C_6$ alkyl, phenyl, benzyl;

$R^{20}$ is H, $C_1$-$C_6$ alkyl, phenyl, benzyl, —C(O)R$^6$ or —SO$_2$R$^6$;

$R^{21}$ is 1 to 3 moieties independently selected from the group consisting of H, —CN, —CF$_3$, —OCF$_3$, halogen, —NO$_2$, $C_1$-$C_6$ alkyl, $C_1$-$C_6$alkoxy, ($C_1$-$C_6$)alkylamino, di-(($C_1$-$C_6$)alkyl)amino, amino($C_1$-$C_6$)alkyl, ($C_1$-$C_6$)-alkylamino($C_1$-$C_6$)alkyl, di-(($C_1$-$C_6$)alkyl)-amino($C_1$-$C_6$)alkyl, hydroxy-($C_1$-$C_6$)alkyl, —COOR$^{17}$, —COR$^{17}$, —NHCOR$^{16}$, —NHSO$_2$R$^{16}$, —NHSO$_2$CH$_2$CF$_3$, heteroaryl, —C(=NOR$^{17}$)R$^{18}$, NR$^{25}$R$^{26}$alkyl-, hydroxyalkyl-, —C(O)OR$^{17}$, —COR$^{17}$, —NHCOR$^{16}$, —NHS(O)$_2$R$^{16}$, —NHS(O)$_2$CH$_2$CF$_3$, —C(O)NR$^{25}$R$^{26}$—NR$^{25}$—C(O)—NR$^{25}$R$^{26}$, —S(O)R$^{13}$, —S(O)$_2$R$^{13}$ and —SR$^{13}$;

$R^{22}$ is selected from the group consisting of H, $R^{24}$—($C_1$-$C_{10}$)alkyl, $R^{24}$—($C_2$-$C_{10}$)alkenyl, $R^{24}$($C_2$-$C_{10}$)alkynyl, $R^{27}$-heterocycloalkyl, $R^{25}$-aryl, $R^{25}$-aryl($C_1$-$C_6$)alkyl, $R^{29}$—($C_3$-$C_7$)cycloalkyl, $R^{29}$—($C_3$-$C_7$)cycloalkenyl, —OH, —OC(O)R$^{30}$, —C(O)OR$^{30}$, —C(O)R$^{30}$, —C(C)NR$^{30}$R$^{31}$, —NR$^{30}$R$^{31}$, —NR$^{30}$C(O)R$^{31}$, —NR$^{30}$C(O)NR$^{31}$R$^{32}$, NHSO$_2$R$^{30}$, —OC(O)NR$^{30}$R$^{31}$, $R^{24}$—($C_1$-$C_{10}$)alkoxy, $R^{24}$—($C_2$-$C_{10}$)-alkenyloxy, $R^{24}$—($C_2$-$C_{10}$)alkynyloxy, $R^{27}$-heterocycloalkyloxy, $R^{29}$—($C_3$-$C_7$)cycloalkyloxy, $R^{29}$—($C_3$-$C_7$)cyclo-alkenyloxy, $R^{29}$—($C_3$-$C_7$)cycloalkyl-NH—, —NHSO$_2$NHR$^{16}$ and —CH(=NOR$^{17}$);

or $R^{22}$ and $R^{10}$ together with the carbon to which they are attached, independently form a $R^{42}$-substituted carbocyclic ring of 3-10 atoms, or a $R^{42}$-substituted heterocyclic ring of 4-10 atoms wherein 1-3 ring members are independently selected from the group consisting of —O—, —NH— and —SOn$_2$-, provided that when $R^{22}$ and $R^{10}$ form a ring, the single-dashed line represents an absent bond;

$R^{24}$ is 1, 2 or 3 moieties independently selected from the group consisting of H, halogen, —OH, ($C_1$-$C_6$)alkoxy, $R^{35}$-aryl, ($C_1$-$C_{10}$)-alkyl-C(O)—, ($C_2$-$C_{10}$)-alkenyl-C(O)—, ($C_2$-$C_{10}$)alkynyl-C(O), heterocycloalkyl, $R^{26}$—($C_3$-$C_7$)cycloalkyl, $R^{26}$—($C_3$-$C_7$)cycloalkenyl, —OC(O)R$^{30}$, —C(O)OR$^{30}$, —C(O)R$^{30}$, —C(O)NR$^{30}$R$^{31}$, —NR$^{30}$R$^{31}$, —NR$^{30}$C(O)R$^{31}$, —NR$^{30}$C(O)NR$^{31}$R$^{32}$, —NHSO$_2$R$^{30}$, —OC(O)NR$^{30}$R$^{31}$, $R^{24}$—($C_2$-$C_{10}$)-alkenyloxy, $R^{24}$—($C_2$-$C_{10}$)alkynyloxy, $R^{27}$-heterocycloalkyloxy, $R^{29}$—($C_3$-$C_7$)-cycloalkyloxy, $R^{29}$—($C_3$-$C_7$)cyclo-alkenyloxy, $R^{29}$—($C_3$-$C_7$)cycloalkyl-NH—, —NHSO$_2$NHR$^{16}$ and —CH(=NOR$^{17}$);

$R^{25}$ is 1, 2 or 3 moieties independently selected from the group consisting of H, heterocycloalkyl, halogen, —COOR$^{36}$, —CN, —C(O)NR$^{37}$R$^{38}$, —NR$^{39}$C(O)R$^{40}$, —OR$^{36}$, ($C_3$-$C_7$)cycloalkyl, ($C_3$-$C_7$)cycloalkyl-$C_1$-$C_6$) alkyl, ($C_1$-$C_6$)alkyl($C_3$-$C_7$)cycloalkyl-($C_1$-$C_6$)alkyl, halo($C_1$-$C_6$)alkyl($C_3$-$C_7$)cycloalkyl($C_1$-$C_6$)alkyl, hydroxy($C_1$-$C_6$)alkyl, ($C_1$-$C_6$)alkoxy($C_1$-$C_6$)alkyl, and $R^{41}$-heteroaryl; or two $R^{25}$ groups on adjacent ring carbons form a fused methylenedioxy group;

$R^{26}$ is 1, 2, or 3 moieties independently selected from the group consisting of H, halogen and ($C_1$-$C_6$) alkoxy;

$R^{27}$ is 1, 2 or 3 moieties independently selected from the group consisting of H, $R^{28}$—($C_1$-$C_{10}$)alkyl, $R^{28}$—($C_2$-$C_{10}$)alkenyl, and $R^{28}$—($C_2$-$C_{10}$)alkynyl;

$R^{28}$ is H, —OH or ($C_1$-$C_6$) alkoxy;

$R^{29}$ is 1, 2 or 3 moieties independently selected from the group consisting of H, $(C_1-C_6)$alkyl, —OH, $(C_1-C_6)$alkoxy and halogen;

$R^{30}$, $R^{31}$ and $R^{32}$ are independently selected from the group consisting of H, $(C_1-C_{10})$-alkyl, $(C_1-C_6)$alkoxy$(C_1-C_{10})$-alkyl, $R^{25}$-aryl$(C_1-C_6)$—alkyl, $R^{33}$—$(C_3-C_7)$cycloalkyl, $R^{34}$—$(C_3-C_7)$cycloalkyl$(C_1-C_6)$alkyl, $R^{25}$-aryl, heterocycloalkyl, heteroaryl, heterocycloalkyl$(C_1-C_6)$alkyl and heteroaryl$(C_1-C_6)$alkyl;

$R^{33}$ is H, $(C_1-C_6)$alkyl, OH—$(C_1-C_6)$alkyl or $(C_1-C_6)$alkoxy;

$R^{34}$ is (H, $R^3$), (H, $R^{43}$), (O) or (NOR$^{17}$) when the single-dashed line is a single bond; $R^{34}$ is $R^{44}$ when the single-dashed line is a double bond;

$R^{35}$ is 1 to 4 moieties independently selected from the group consisting of H, $(C_1-C_6)$alkyl, —OH, halogen, —CN, $(C_1-C_6)$alkoxy, trihalo$(C_1-C_6)$alkoxy, $(C_1-C_6)$alkylamino, di$((C_1-C_6)$alkyl)amino, —OCF$_3$, OH—$(C_1-C_6)$alkyl, —CHO, —C(O)$(C_1-C_6)$-alkylamino, —C(O)di$((C_1-C_6)$alkyl)amino, —NH$_2$, —NHC(O)$(C_1-C_6)$alkyl and —N$((C_1-C_6)$alkyl)C(O)$(C_1-C_6)$alkyl;

$R^{36}$ is H, $(C_1-C_6)$alkyl, halo$(C_1-C_6)$alkyl, dihalo$(C_1-C_6)$alkyl or trifluoro$(C_1-C_6)$alkyl;

$R^{37}$ and $R^{38}$ are independently selected from the group consisting of H, $(C_1-C_6)$alkyl, aryl$(C_1-C_6)$alkyl, phenyl and $(C_3-C_{15})$cycloalkyl;

or $R^{37}$ and $R^{38}$ together are —(CH$_2$)$_4$—, —(CH$_2$)$_5$— or —(CH$_2$)$_2$—NR$^{39}$—(CH$_2$)$_2$— and form a ring with the nitrogen to which they are attached;

$R^{39}$ and $R^{40}$ are independently selected from the group consisting of H, $(C_1-C_6)$alkyl, aryl$(C_1-C_6)$alkyl, phenyl and $(C_3-C_{15})$-cycloalkyl;

or $R^{39}$ and $R^{40}$ in the group —NR$^{39}$C(O)R$^{40}$, together with the carbon and nitrogen atoms to which they are attached, form a cyclic lactam having 5-8 ring members;

$R^{41}$ is 1 to 4 moieties independently selected from the group consisting of H, $(C_1-C_6)$alkyl, $(C_1-C_6)$alkoxy, $(C_1-C_6)$alkylamino, di$((C_1-C_6)$alkyl)amino, —OCF$_3$, OH—$(C_1-C_6)$alkyl, —CHO and phenyl;

$R^{42}$ is 1 to 3 moieties independently selected from the group consisting of hydrogen, —OH, $(C_1-C_6)$alkyl and $(C_1-C_6)$alkoxy;

$R^{43}$ is —NR$^{30}$R$^{31}$, —NR$^{30}$C(O)R$^{31}$, —NR$^{30}$C(O)NR$^{31}$R$^{32}$, —NHSO$_2$R$^{30}$ or —NHCOOR$^{17}$;

$R^{44}$ is H, $C_1-C_6$ alkoxy, —SOR$^{16}$, —SO$_2$R$^{17}$, —C(O)OR$^{17}$, —C(O)NR$^{18}$R$^{19}$, $C_1-C_6$ alkyl, halogen, fluoro$(C_1-C_6)$alkyl, difluoro$(C_1-C_6)$alkyl, trifluoro$(C_1-C_6)$alkyl, $C_3-C_7$ cycloalkyl, $C_2-C_6$ alkenyl, aryl$(C_1-C_6)$alkyl, aryl$(C_2-C_6)$alkenyl, heteroaryl$(C_1-C_6)$alkyl, heteroaryl$(C_2-C_6)$alkenyl, hydroxy$(C_1-C_6)$alkyl, amino$(C_1-C_6)$alkyl, aryl, thio$(C_1-C_6)$alkyl, $(C_1-C_6)$alkoxy$(C_1-C_6)$alkyl or $(C_1-C_6)$alkylamino$(C_1-C_6)$alkyl; and $R^{45}$ is H, $C_1-C_6$ alkyl, —COOR$^{16}$ or —SO$_2$.

2. A compound of claim 1 wherein W is phenyl.

3. A compound of claim 2 wherein W is substituted by fluoro.

4. A compound of claim 2 wherein W is substituted by —CN.

5. A compound of claim 1 wherein Z is —CH$_2$— and $n_1$ is 1.

6. A compound of claim 1 wherein Z is —O— and $n_1$ is 1.

7. A compound of claim 1 wherein Z is —O— and $n_1$ is 1.

8. A compound of claim 1 wherein R1 is methyl, and $R^2$, $R^8$, $R^9$, $R^{10}$, $R^{11}$ are all H.

9. A compound of claim 1 wherein $R^3$ is H.

10. A compound of claim 1 wherein $R^3$ is —OH.

11. A compound of claim 1 wherein $R^{22}$ is methyl.

12. A compound of claim 1 wherein Y is O.

13. A compound of claim 1 wherein the single-dashed line represents a single bond.

14. A pharmaceutical composition comprising at least one compound of claim 1 and a pharmaceutically acceptable carrier.

15. A compound represented by a structural formula selected from the group consisting of:

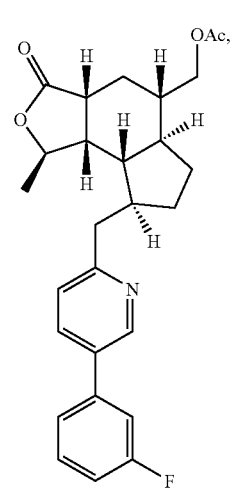

3

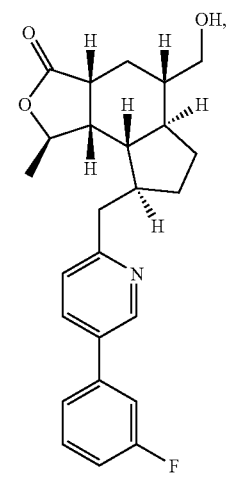

4

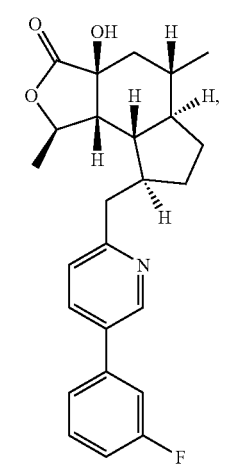

5

-continued
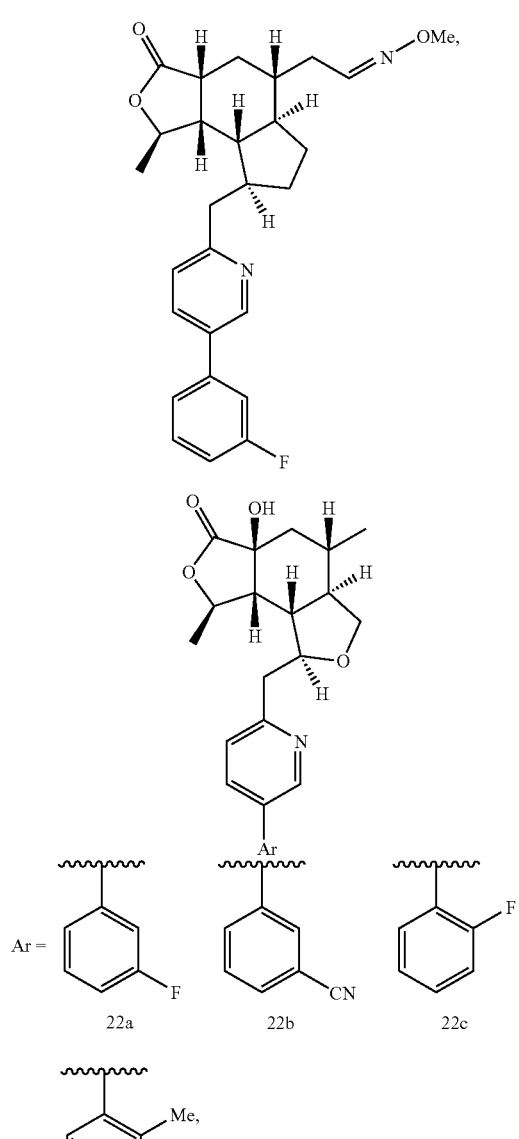
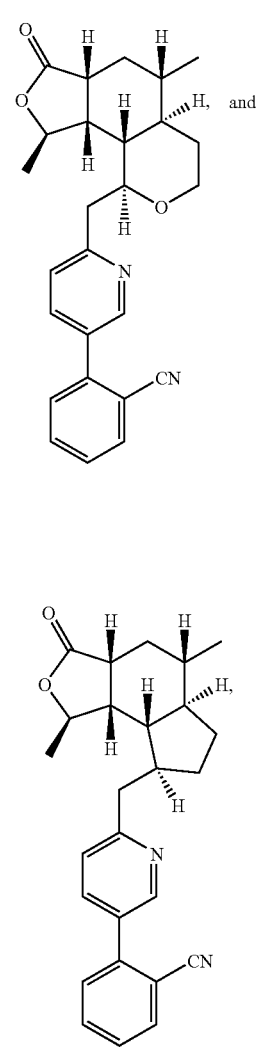
or a pharmaceutically acceptable salt or solvate thereof.
* * * * *

UNITED STATES PATENT AND TRADEMARK OFFICE
CERTIFICATE OF CORRECTION

PATENT NO.         : 7,442,712 B2
APPLICATION NO.    : 11/137283
DATED              : October 28, 2008
INVENTOR(S)        : Mariappan V. Chelliah et al.

It is certified that error appears in the above-identified patent and that said Letters Patent is hereby corrected as shown below:

In the Claims:

Claim 1, column 38, line 24, at end of line, delete "-C(C)" and insert "C(O)"

Claim 1, column 38, line 26, insert -- - -- after "NR31R32,"

Claim 7, column 39, line 62, at end of line, delete "1" and insert -- 2 --

Claim 14, column 40, line 5, insert -- a therapeutically effective amount of -- after the word "comprising".

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO.        : 7,442,712 B2
APPLICATION NO. : 11/137283
DATED             : October 28, 2008
INVENTOR(S)      : Chelliah et al.

It is certified that error appears in the above-identified patent and that said Letters Patent is hereby corrected as shown below:

Column 36, line 45, Claim 1 should read:

1. A compound represented by the structural formula

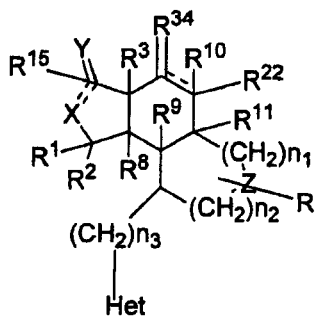

Formula 1 or a pharmaceutically acceptable salt or solvate thereof, wherein:

the single-dashed line ---- between the ring carbons to which $R^{10}$ and $R^{34}$ are attached represents either a single bond or a double bond;

the double-dashed line = = = = between X and the carbon to which Y is attached represents a single bond;

X is -O-;

$R^{15}$ is H, or $C_1$-$C_6$alkyl;

Y is (O), (S), (H, H), (H, OH) or (H, $C_1$-$C_6$ alkoxy);

Z is selected from the group consisting of -$CH_2$- and -O-;

Signed and Sealed this

Fourteenth Day of December, 2010

David J. Kappos
*Director of the United States Patent and Trademark Office*

$n_1$ is 1 or 2;

$n_2$ is 0;

$n_3$ is 1;

$n_4$ is 0, 1 or 2;

R is 1 to 3 substituents independently selected from the group
consisting of H, $C_1$-$C_6$ alkyl, halogen, hydroxy, amino, ($C_1$-$C_6$) alkyl-amino, ($C_1$-$C_6$)dialkylamino, ($C_1$-$C_6$)alkoxy, -$COR^{16}$, -$COOR^{17}$, -$SOR^{16}$, -$SO_2R^{16}$, - $NR^{16}COR^{16a}$, -$NR^{16}COOR^{16a}$, -$NR^{16}CONR^4R^5$, fluoro-($C_1$-$C_6$)alkyl, difluoro($C_1$-$C_6$)alkyl, trifluoro($C_1$-$C_6$)alkyl, $C_3$-$C_6$ cycloalkyl, $C_2$-$C_6$ alkenyl, aryl($C_1$-$C_6$)alkyl, aryl($C_2$-$C_6$)alkenyl, heteroaryl($C_1$-$C_6$)-alkyl, heteroaryl($C_2$-$C_6$)alkenyl, hydroxy($C_1$-$C_6$)alkyl, amino($C_1$-$C_6$)-alkyl, aryl and thio($C_1$-$C_6$)alkyl;

$R^1$ and $R^2$ are independently selected from the group consisting of H,
$C_1$-$C_6$ alkyl, fluoro($C_1$-$C_6$)alkyl, difluoro($C_1$-$C_6$)alkyl, trifluoro-($C_1$-$C_6$)alkyl, $C_3$-$C_7$ cycloalkyl, $C_2$-$C_6$ alkenyl, aryl($C_1$-$C_6$)alkyl, aryl($C_2$-$C_6$)alkenyl, heteroaryl($C_1$-$C_6$)alkyl, heteroaryl($C_2$-$C_6$)alkenyl, hydroxy-($C_1$-$C_6$)alkyl, ($C_1$-$C_6$)alkoxy($C_1$-$C_6$)alkyl, amino-($C_1$-$C_6$)alkyl, aryl and thio($C_1$-$C_6$)alkyl; or $R^1$ and $R^2$ together form a =O group;

$R^3$ is H, hydroxy, $C_1$-$C_6$ alkoxy, -$NR^{18}R^{19}$, -$SOR^{16}$, -$SO_2R^{17}$,
-$C(O)OR^{17}$, -$C(O)NR^{18}R^{19}$, $C_1$-$C_6$ alkyl, halogen, fluoro($C_1$-$C_6$)alkyl, difluoro($C_1$-$C_6$)alkyl, trifluoro($C_1$-$C_6$)alkyl, $C_3$-$C_7$ cycloalkyl, $C_2$-$C_6$ alkenyl, aryl($C_1$-$C_6$)alkyl, aryl($C_2$-$C_6$)alkenyl, heteroaryl($C_1$-$C_6$)alkyl, heteroaryl($C_2$-$C_6$)alkenyl, hydroxy($C_1$-$C_6$)alkyl, amino($C_1$-$C_6$)alkyl, aryl, thio($C_1$-$C_6$)alkyl, ($C_1$-$C_6$)alkoxy($C_1$-$C_6$)alkyl or ($C_1$-$C_6$)alkylamino($C_1$-$C_6$)alkyl, -O-aryl, $N_3$, $NO_2$, $C(=NR^1)NR^1R^2$, $N=C(R^1)NR^1R^2$, $NR^{18}COR^{19}$, $NR^{18}CONR^{18}R^{19}$, $NR^{18}C(O)OR^{19}$, $NR^{18}S(O)_2R^{19}$, $NR^{18}S(O)_2NR^{18}R^{19}$, $NHNR^{18}R^{19}$, $NR^{18}NR^{18}R^{19}$ or $NR^{18}R^{19}$;

Het is pyridyl, wherein the Het group is optionally substituted by W, wherein W is
selected from the group consisting of aryl optionally substituted by halo or CN;

$R^4$ and $R^5$ are independently selected from the group consisting of H, $C_1$-$C_6$ alkyl, phenyl, benzyl and $C_3$-$C_7$ cycloalkyl, or $R^4$ and $R^5$ together are -$(CH_2)_4$-, -$(CH_2)_5$- or -$(CH_2)_2NR^7$-$(CH_2)_2$- and form a heterocyclyl ring with the nitrogen to which they are attached;

$R^6$ is independently selected from the group consisting of H, $C_1$-$C_6$ alkyl, phenyl, $(C_3$-$C_7)$cycloalkyl, $(C_3$-$C_7)$cycloalkyl$(C_1$-$C_6)$alkyl, $(C_1$-$C_6)$alkoxy$(C_1$-$C_6)$alkyl, hydroxy$(C_1$-$C_6)$alkyl and amino$(C_1$-$C_6)$alkyl;

$R^7$ is H or $(C_1$-$C_6)$alkyl;

$R^8$, $R^{10}$ and $R^{11}$ are independently selected from the group consisting of $R^1$ and -$OR^1$, provided that when the single-dashed line is a double bond, $R^{10}$ is absent;

$R^9$ is H, OH, $C_1$-$C_6$ alkoxy, halogen or halo$(C_1$-$C_6)$alkyl;

$R^{16}$ and $R^{16a}$ are independently selected from the group consisting of $C_1$-$C_6$ lower alkyl, phenyl or benzyl;

$R^{17}$, $R^{18}$ and $R^{19}$ are independently selected from the group consisting of H, $C_1$-$C_6$ alkyl, phenyl, benzyl;

$R^{20}$ is H, $C_1$-$C_6$ alkyl, phenyl, benzyl, -$C(O)R^6$ or -$SO_2R^6$;

$R^{21}$ is 1 to 3 moieties independently selected from the group consisting of H, -CN, -$CF_3$, -$OCF_3$, halogen, -$NO_2$, $C_1$-$C_6$ alkyl, $C_1$-$C_6$alkoxy, $(C_1$-$C_6)$alkylamino, di-$((C1$-$C6)$alkyl)amino, amino$(C_1$-$C_6)$alkyl, $(C_1$-$C_6)$-alkylamino$(C_1$-$C_6)$alkyl, di-$((C_1$-$C_6)$alkyl)-amino$(C_1$-$C_6)$alkyl, hydroxy-$(C_1$-$C_6)$alkyl, -$COOR^{17}$, -$COR^{17}$, -$NHCOR^{16}$, -$NHSO_2R^{16}$, -$NHSO_2CH_2CF_3$, heteroaryl, -$C(=NOR^{17})R^{18}$, $NR^{25}R^{26}$alkyl-, hydroxy-alkyl-, -$C(O)OR^{17}$, -$COR^{17}$, -$NHCOR^{16}$, -$NHS(O)_2R^{16}$, -$NHS(O)_2CH_2CF_3$, -$C(O)NR^{25}R^{26}$, -$NR^{25}$-$C(O)$-$NR^{25}R^{26}$, -$S(O)R^{13}$, -$S(O)_2R^{13}$ and -$SR^{13}$;

$R^{22}$ is selected from the group consisting of H, $R^{24}$-$(C_1$-$C_{10})$alkyl, $R^{24}$-$(C_2$-$C_{10})$alkenyl, $R^{24}$-$(C_2$-$C_{10})$alkynyl, $R^{27}$-hetero-cycloalkyl, $R^{25}$-aryl, $R^{25}$-aryl$(C_1$-$C_6)$alkyl, $R^{29}$-$(C_3$-$C_7)$cycloalkyl, $R^{29}$-$(C_3$-$C_7)$cycloalkenyl,

-OH, -OC(O)$R^{30}$, -C(O)O$R^{30}$, -C(O)$R^{30}$,

-C(O)N$R^{30}R^{31}$, -N$R^{30}R^{31}$, -N$R^{30}$C(O)$R^{31}$, -N$R^{30}$C(O)N$R^{31}R^{32}$,

-NHSO$_2R^{30}$, -OC(O)N$R^{30}R^{31}$, $R^{24}$-$(C_1$-$C_{10})$alkoxy, $R^{24}$-$(C_2$-$C_{10})$-alkenyloxy, $R^{24}$-$(C_2$-$C_{10})$alkynyloxy, $R^{27}$-heterocycloalkyloxy, $R^{29}$-$(C_3$-$C_7)$cycloalkyloxy, $R^{29}$-$(C_3$-$C_7)$cyclo-alkenyloxy, $R^{29}$-$(C_3$-$C_7)$cycloalkyl-NH-, -NHSO$_2$NH$R^{16}$ and -CH(=NO$R^{17}$);

or $R^{22}$ and $R^{10}$ together with the carbon to which they are attached, independently form a $R^{42}$-substituted carbocyclic ring of 3-10 atoms, or a $R^{42}$-substituted heterocyclic ring of 4-10 atoms wherein 1-3 ring members are independently selected from the group consisting of -O-, -NH- and -SOn$_2$-, provided that when $R^{22}$ and $R^{10}$ form a ring, the single-dashed line represents an absent bond;

$R^{24}$ is 1, 2 or 3 moieties independently selected from the group consisting of H, halogen, -OH, $(C_1$-$C_6)$alkoxy, $R^{35}$-aryl, $(C_1$-$C_{10})$-alkyl-C(O)-, $(C_2$-$C_{10})$-alkenyl-C(O)-, $(C_2$-$C_{10})$alkynyl-C(O), heterocycloalkyl, $R^{26}$-$(C_3$-$C_7)$cycloalkyl, $R^{26}$-$(C_3$-$C_7)$cycloalkenyl, -OC(O)$R^{30}$, -C(O)O$R^{30}$, -C(O)$R^{30}$, -C(O)N$R^{30}R^{31}$, -N$R^{30}R^{31}$, -N$R^{30}$C(O)$R^{31}$, -N$R^{30}$C(O)N$R^{31}R^{32}$, -NHSO$_2R^{30}$, -OC(O)N$R^{30}R^{31}$, $R^{24}$-$(C_2$-$C_{10})$-alkenyloxy, $R^{24}$-$(C_2$-$C_{10})$alkynyloxy, $R^{27}$-heterocycloalkyloxy, $R^{29}$-$(C_3$-$C_7)$-cycloalkyloxy, $R^{29}$-$(C_3$-$C_7)$cyclo-alkenyloxy, $R^{29}$-$(C_3$-$C_7)$cycloalkyl-NH-, -NHSO$_2$NH$R^{16}$ and -CH(=NO$R^{17}$);

$R^{25}$ is 1, 2 or 3 moieties independently selected from the group consisting of H, heterocycloalkyl, halogen, -COO$R^{36}$, -CN, -C(O)N$R^{37}R^{38}$, -N$R^{39}$C(O)$R^{40}$, -O$R^{36}$, $(C_3$-$C_7)$cycloalkyl, $(C_3$-$C_7)$cycloalkyl-$C_1$-$C_6)$alkyl, $(C_1$-$C_6)$alkyl, $(C_3$-$C_7)$cycloalkyl-$(C_1$-$C_6)$alkyl, halo$(C_1$-$C_6)$alkyl$(C_3$-$C_7)$cycloalkyl $(C_1$-$C_6)$alkyl, hydroxy $(C_1$-$C_6)$alkyl, $(C_1$-$C_6)$alkoxy$(C_1$-$C_6)$alkyl, and $R^{41}$-heteroaryl; or two $R^{25}$ groups on adjacent ring carbons form a fused methylenedioxy group;

$R^{26}$ is 1, 2, or 3 moieties independently selected from the group consisting of H, halogen and $(C_1-C_6)$ alkoxy;

$R^{27}$ is 1, 2 or 3 moieties independently selected from the group consisting of H, $R^{28}$-$(C_1-C_{10})$alkyl, $R^{28}$-$(C_2-C_{10})$alkenyl, and $R^{28}$-$(C_2-C_{10})$alkynyl;

$R^{28}$ is H, -OH or $(C_1-C_6)$ alkoxy;

$R^{29}$ is 1, 2 or 3 moieties independently selected from the group consisting of H, $(C_1-C_6)$alkyl, -OH, $(C_1-C_6)$alkoxy and halogen;

$R^{30}$, $R^{31}$ and $R^{32}$ are independently selected from the group consisting of H, $(C_1-C_{10})$-alkyl, $(C_1-C_6)$alkoxy$(C_1-C_{10})$-alkyl, $R^{25}$-aryl$(C_1-C_6)$-alkyl, $R^{33}$-$(C_3-C_7)$cycloalkyl, $R^{34}$-$(C_3-C_7)$cycloalkyl$(C_1-C_6)$alkyl, $R^{25}$-aryl, heterocycloalkyl, heteroaryl, heterocycloalkyl$(C_1-C_6)$alkyl and heteroaryl$(C_1-C_6)$alkyl;

$R^{33}$ is H, $(C_1-C_6)$alkyl, OH-$(C_1-C_6)$alkyl or $(C_1-C_6)$alkoxy;

$R^{34}$ is (H, $R^3$), (H, $R^{43}$), (O) or (NOR$^{17}$) when the single-dashed line is a single bond; $R^{34}$ is $R^{44}$ when the single-dashed line is a double bond;

$R^{35}$ is 1 to 4 moieties independently selected from the group consisting of

H, $(C_1-C_6)$alkyl, -OH, halogen, -CN, $(C_1-C_6)$alkoxy, trihalo$(C_1-C_6)$alkoxy, $(C_1-C_6)$alkylamino, di$((C_1-C_6)$alkyl)amino, -OCF$_3$, OH-$(C_1-C_6)$alkyl, -CHO, -C(O)$(C_1-C_6)$-alkylamino, -C(O)di$((C_1-C_6)$alkyl)amino, -NH$_2$, -NHC(O)$(C_1-C_6)$alkyl and -N$((C_1-C_6)$alkyl)C(O)$(C_1-C_6)$alkyl;

$R^{36}$ is H, $(C_1-C_6)$alkyl, halo$(C_1-C_6)$alkyl, dihalo$(C_1-C_6)$alkyl or trifluoro$(C_1-C_6)$alkyl;

$R^{37}$ and $R^{38}$ are independently selected from the group consisting of H, $(C_1-C_6)$alkyl, aryl$(C_1-C_6)$alkyl, phenyl and $(C_3-C_{15})$cycloalkyl;

or $R^{37}$ and $R^{38}$ together are -(CH$_2$)$_4$-, -(CH$_2$)$_5$- or -(CH$_2$)$_2$-NR$^{39}$-(CH$_2$)$_2$- and form a ring with the nitrogen to which they are attached;

$R^{39}$ and $R^{40}$ are independently selected from the group consisting of H, $(C_1-C_6)$alkyl, aryl$(C_1-C_6)$alkyl, phenyl and $(C_3-C_{15})$-cycloalkyl;

or $R^{39}$ and $R^{40}$ in the group -NR$^{39}$C(O)R$^{40}$, together with the carbon and nitrogen atoms to which they are attached, form a cyclic lactam having 5-8 ring members;

$R^{41}$ is 1 to 4 moieties independently selected from the group consisting of
   H, $(C_1\text{-}C_6)$alkyl, $(C_1\text{-}C_6)$alkoxy, $(C_1\text{-}C_6)$alkylamino, di($(C_1\text{-}C_6)$alkyl)amino, $-OCF_3$, $OH\text{-}(C_1\text{-}C_6)$alkyl, -CHO and phenyl;

$R^{42}$ is 1 to 3 moieties independently selected from the group consisting of
   hydrogen, -OH, $(C_1\text{-}C_6)$alkyl and $(C_1\text{-}C_6)$alkoxy;

$R^{43}$ is $-NR^{30}R^{31}$, $-NR^{30}C(O)R^{31}$, $-NR^{30}C(O)NR^{31}R^{32}$, $-NHSO_2R^{30}$ or $-NHCOOR^{17}$;

$R^{44}$ is H, $C_1\text{-}C_6$ alkoxy, $-SOR^{16}$ $-SO_2R^{17}$, $-C(O)OR^{17}$, $-C(O)NR^{18}R^{19}$,
   $C_1\text{-}C_6$ alkyl, halogen, fluoro$(C_1\text{-}C_6)$alkyl, difluoro$(C_1\text{-}C_6)$alkyl,
   trifluoro$(C_1\text{-}C_6)$alkyl, $C_3\text{-}C_7$ cycloalkyl, $C_2\text{-}C_6$ alkenyl,
   aryl$(C_1\text{-}C_6)$alkyl, aryl$(C_2\text{-}C_6)$alkenyl, heteroaryl$(C_1\text{-}C_6)$alkyl,
   heteroaryl$(C_2\text{-}C_6)$alkenyl, hydroxy$(C_1\text{-}C_6)$alkyl, amino$(C_1\text{-}C_6)$alkyl,
   aryl, thio$(C_1\text{-}C_6)$alkyl, $(C_1\text{-}C_6)$alkoxy$(C_1\text{-}C_6)$alkyl or
   $(C_1\text{-}C_6)$alkylamino$(C_1\text{-}C_6)$alkyl; and $R^{45}$ is H, $C_1\text{-}C_6$ alkyl, $-COOR^{16}$ or $-SO_2$.

Please replace Claim 7 in its entirety with:

Claim 7. A compound of claim 1 wherein Z is –O– and $n_1$ is 2.